(12) United States Patent
Napier et al.

(10) Patent No.: US 7,601,889 B2
(45) Date of Patent: Oct. 13, 2009

(54) ELONGASE GENE AND PRODUCTION OF Δ9-POLYUNSATURATED FATTY ACIDS

(76) Inventors: Johnathan A. Napier, 40, The Nursery, Bedminster, Bristol BS3 3EB (GB); Colin M. Lazarus, 119 York Road, Montpelier, Bristol BS6 5QG (GB); Baoxiu Qi, 4 Cumberland House, Norfolk Crescent, Bath BA1 2BG (GB); Jens Lerchl, Onsjövägen 17, 26831 Svalöv (SE)

( * ) Notice: Subject to any disclaimer, the term of this patent is extended or adjusted under 35 U.S.C. 154(b) by 128 days.

(21) Appl. No.: 10/472,321

(22) PCT Filed: Mar. 26, 2002

(86) PCT No.: PCT/EP02/03418

§ 371 (c)(1),
(2), (4) Date: Sep. 22, 2003

(87) PCT Pub. No.: WO02/077213

PCT Pub. Date: Oct. 3, 2002

(65) Prior Publication Data

US 2005/0089981 A1  Apr. 28, 2005

(30) Foreign Application Priority Data

Mar. 26, 2001 (GB) ............................ 0107510.1

(51) Int. Cl.
*C07H 21/04* (2006.01)
*C12N 15/00* (2006.01)
*C12N 5/04* (2006.01)
*C12N 9/10* (2006.01)

(52) U.S. Cl. .................... 800/281; 435/320.1; 435/193; 435/419; 536/23.2

(58) Field of Classification Search ........................ None
See application file for complete search history.

(56) References Cited

U.S. PATENT DOCUMENTS

| | | | |
|---|---|---|---|
| 4,873,316 A | 10/1989 | Meade et al. | |
| 4,962,028 A | 10/1990 | Bedbrook et al. | |
| 4,987,071 A | 1/1991 | Cech et al. | |
| 5,116,742 A | 5/1992 | Cech et al. | |
| 5,169,770 A | 12/1992 | Chee et al. | |
| 5,187,267 A | 2/1993 | Comai et al. | |
| 5,352,605 A | 10/1994 | Fraley et al. | |
| 5,475,099 A | 12/1995 | Knauf et al. | |
| 5,504,200 A | 4/1996 | Hall et al. | |
| 5,608,152 A | 3/1997 | Kridl et al. | |
| 5,850,026 A | 12/1998 | DeBonte et al. | |
| 6,043,111 A | 3/2000 | Furuse | |
| 6,051,754 A | 4/2000 | Knutzon | |
| 6,140,486 A | 10/2000 | Facciotti et al. | |

FOREIGN PATENT DOCUMENTS

| | | |
|---|---|---|
| CA | 2007091 | 6/1990 |
| EP | 264 166 | 4/1988 |
| EP | 322 783 | 7/1989 |
| EP | 388 186 | 9/1990 |
| EP | 397 687 | 11/1990 |
| WO | 84/02913 | 8/1984 |
| WO | 91/13980 | 9/1991 |
| WO | 93/21334 | 10/1993 |
| WO | 95/15389 | 6/1995 |
| WO | 95/16783 | 6/1995 |
| WO | 95/18222 | 6/1995 |
| WO | 95/19443 | 7/1995 |
| WO | 95/23230 | 8/1995 |
| WO | 97/96250 | 2/1997 |
| WO | 2007/020078 | 6/1997 |
| WO | 98/13487 | 4/1998 |
| WO | 98/45461 | 10/1998 |
| WO | 98/46764 | 10/1998 |
| WO | 98/46765 | 10/1998 |
| WO | 98/46776 | 10/1998 |
| WO | 99/16890 | 4/1999 |
| WO | 99/33958 | 7/1999 |
| WO | 99/46394 | 9/1999 |
| WO | 99/64616 | 12/1999 |
| WO | 00/12720 | 3/2000 |
| WO | 00/34439 | 6/2000 |
| WO | 00/55330 | 9/2000 |
| WO | 01/59128 | 8/2001 |
| WO | 02/08401 | 1/2002 |

OTHER PUBLICATIONS

XP-002200201, Beaudoin et al., PNAS, Jun. 6, 2000, vol. 97, No. 12 6421-6426.

(Continued)

*Primary Examiner*—Nashaat T Nashed
*Assistant Examiner*—Md. Younus Meah
(74) *Attorney, Agent, or Firm*—Novak Druce + Quigg LLP

(57) ABSTRACT

This invention relates to a new elongase gene having the sequence SEQ ID NO: 1 or its derivatives, to a gene construct comprising this sequence or its derivatives and to its use. The inventive nucleic acid sequence encodes a polypeptide which elongates α-linolenic acid ($C_{18:3\ \Delta 9,12,15}$) by at least two carbon atoms whereas γ-linolenic acid ($C_{18:3\ \Delta 6,9,12}$) is not elongated. The invention additionally relates to vectors or organisms comprising an elongase gene having the sequence SEQ ID NO: 1 or its derivatives.

The invention further relates to a process for the production of polyunsaturated fatty acids (=PUFAs) with an organism which comprises the elongase gene and which organism produces high amounts of oils and especially oils with a high content of unsaturated fatty acids. Additionally the invention relates to an oil and/or fatty acid composition with a higher content of polyunsaturated $C_{20}$ or $C_{22}$ fatty acids with at least two double bonds and/or to a triacylglycerol composition with a higher content of said polyunsaturated fatty acids.

13 Claims, 6 Drawing Sheets

OTHER PUBLICATIONS

XP-002200200,Parker-Barnes et al.,PNAAS,Jul. 18, 2000,vol. 97.
XP-002200199,Sevilla et al., Appl.Microbiol Biotechnol (1998) 50: 199-205 No. 15 8284-8289.
XP-001071204, Medina et al., JAOCS, vol. 72,No. 5, (1995).
FEBS Ltrs. 510(2002)159-165, Qi et al.
Mar.Biotechnol 1, 239-251,1999, Falciatore, Transformation of Nonselectable Reporter Genes in Marine Diatoms.
J.Phycol.31,1004-1012(1995)Dunahay et al., Genetic transformation of the Diatoms Cyclotella Cryptica and Navicula Saprophila.
MolGenGenet(1991)225:459-467, Baumlein et al.,A Novel Seed Protein from Vicia faba is developmentally regulated in transgenic tobacco and Arabidopsis plants.
FEBS 08632,vol. 268,No. 2,427-430,Mol et al., Regulation of Plant gene expression by antisense RNA Nucleic Acids Res. 1999,vol. 27,No. 5,1323-1330.
Cole-Strauss et al. Targeted gene repair directed by the chimeric RNA/DNA oligonucleotide in a mammalian cell-free extract Gene Therapy,Kmiec,American Scientist, vol. 87,240-247.
Cell,vol. 5,503-512,Nov. 6, 1987, Thomas et al., Site-Directed Mutagenesis by gene targeting in Mouse Embryo-derived stem cells.
Proc.Natl.Acad.Sci,vol. 95,4368-4373,Apr. 1998,Strepp et al., Plant nuclear gene knockout reveals a role in plastid division for the homolog of the bacterial cell division protein FtsZ, an ancestral tubulin.
J.Mol.Biol.(1996)263,359-368,Ott et al., Rational Molecular Design and Genetic Engineering of Herbicide Resistant Crops by Structure Modeling and Site-directed Mutagenesis of Acetohydroxyacid Synthase Tetrahedron vol. 39,No. 9. 1, 3-22, 1983, DNA Synthesis, Narang.
Ann.Rev.Biochem.1984,53:323-56,Itakura al.,Synthesis and use of synthetic oligonucleotides Science,vol. 198,1056-1063,Expression in *Escheichia coli* of a Chemically Synthesized Gene for the Hormone Somatostatin.
Nucleic Acids Res.,vol. 11,No. 2, 1983, Ike et al., 477-488.
Proc.Natl.Acad.Sci.,vol. 89,7811-7815,Aug. 1992,Arkin et al., An algorithm for protein engineering: Simulations of recursive ensemble mutagenesis, Arkin et al.
Protein Eng.,vol. 6,No. 3,327-331,1993, Recursive ensemble mutagenesis, Delagrave et al.
Peroxynitrite: reactive, invasive and enigmatic, Groves, 226-235.
PNAS,Oct. 12, 1999,vol. 96,No. 21,11689-12210,Cahoon et al., Biosynthetic origin of conjugated double bonds: production of fatty acid components of high-value drying oils in transgenic soybean embryos.
Analytical Biochem.152,141-145(1986),Browse et al., Fatty acid composition of leaf lipids determined after combined digestion and fatty acid methyl ester formation from fresh tissue.
Biologia Plantarum 42(2):209-216,1999,El-Sheekh, Stable transformation of the intact cells of chlorella kessleri with high velocity microprojectiles.
MolGenGenet(1996)252:572-579,Apt et al., Stable nuclear transformation of the diatom Phaeodactylum tricornutum.
The Journal of Biological Chemistry, vol. 271,No. 31, Issue of Aug. 2, 18413-18422, 1996, Toke et al., Isolation and Characterization of a Gene Affecting Fatty Acid Elongation in *Saccharomyces cerevisiae*.
Nature genetics,vol. 27,Jan. 2001,Zhang et al., A 5-bp deletion in ELOVL4 is associated with two related forms of autosomal dominant macular dystrophy.
Biochem J.(2000)350,765-770, Leonard et al., Cloning of a human cDNA encoding a novel enzyme involved in the elongation of long-chain polyunsaturated fatty acids.
PNAS,Jul. 18, 2000,vol. 97,No. 15, 8284-8289, Parker-Barnes et al., Identification and Characterization of an enzyme in volved in the elongation of n-6 and n-3 polyunsaturated fatty acids.
Nucleic Acids Res.,vol. 13,No. 13, 1985, Bytebier et al., Efficient octopine Ti plasmid-derived vectors for Agrobacterium-mediated gene transfer to plants.
MolGenGenet(1986)204:383-396,Konez et al., The promoter of Tl-DNA gene 5 controls the tissue-specific expression of chimaeric genes carried by a novel type of Agrobacterium binary vector.
Plant Cell:Reports (1989)8:238 242,Moloney et al., High efficiency transformation of *Brassica napus* using Agrobacterium vectors.
Plant Physiol.(1989)91,694-701,DeBlock et al., Transformation of *Brassica napus* and *Brassica oleracea* Using Agrobacterium tumefaciens and the Expression of the bar and neo Genes in the Transgenic Plants.
PlantCellReports, (1994)13:282-285,Mlynarova et al., High efficiency Agrobacterium-mediated gene transfer to flax.
Molecular Microbiology(1992)6(3),317-326,Boermann et al., Molecular analysis of the *Corynebacterium glutamicum* gdh gene encoding glutamate dehydrogenase3.
Science,vol. 249,Kessel et al., Murine Developmental Control Genes, 374-379.
Annu.Rev.Plant Physiol.Plant Mol. Biol, 1991, 42:205-225, Gene Transfer to Plants.
Gene 67, (1988)31-40, Smith et al., Single-step purification of polypeptides expressed in *Escherichia coli* as fusions with glutathione S-transferase.
Gene, 69(1988)301-315, Amann et al., Tightly regulated tac promoter vectors useful for the expression of unfused and fused proteins in *Escherichia coli*.
Methods in Enzymology,vol. 185, Gene Expression Technology,60-89.
Methods in Enzymology,vol. 185 119-128,Edited by Goeddel, Minimizing Proteolysis.
Nucleic Acids Res.vol. 20,Suppl.2111-2118, Wada et al.,Codon Usage Tabulated from the GenBank genetic sequence data.
EMBO Jrl.,vol. 6,No. 1,229-234,187, Baldari et al.,A novel leader peptide wich allows efficient secretion of a fragment of human interleukin 1β in *Saccoromyces cerevisiae*.
Cell,vol. 30,933-943, Oct. 1982, Kurjan et al.,Structure of a Yeast Pheromone Gene (MFα): A putative α-Factor Precursor Contains Four Tandem Copies of Mature α-Factor.
Molecular and Cellular Bio.,Dec. 1983,2156-2165, Smith et al., Production of Human Beta Interferon in Insect Cells Infected with Baculovirus Expression Vector.
Nature vol. 329, Oct. 1987,Seed, An LFA-3 cDNA encodes a phospholipid-linked membrane protein homologous to its receptor CD2.
Science,vol. 230, Edlund et al., 912-916,Cell-Specific Expression of the Rat Insulin Gene:Evidence for Role of Two Distinct 5'Flanking Elements.
Methods in Plant Molecular Biology and Biotechnology, Procedures for Introducing Foreign DNA into Plants 72-119, Edited by Glick et al.
Science,vol. 258,Nov. 1992, Nikaido et al., Transport Proteins in Bacteria:Common Themes in Their Design,936-942.
Science,vol. 261,Sep. 10, 1993,Bartel et al., 1411-1418, Isolation of New Ribozymes from a Large Pool of Random Sequences.
Biochemistry and Molecular Biology of Membrane and Storage Lipids of Plants, N.Murata and CRSomerville, Eds, 1993, The American Society of Plant Physiologist, Biosynthesis o 'Uncommon' Fatty Acids and Their Incorporation into Triacylglycerols, Stymne, 150-159.

Fig. 1 Pairwise alignment of Isochrysis galbana elongase (Ig_ASE1, upper row) with Mortierella alpina elongase (M.alpinaGlelo, lower row). Identities are shown in bold characters.

```
Ig_ASE1         ................MALANDAGERIWAAVTDPEI...............     20
M.alpinaGlelo   MESIAPFLPSKMPQDLFMDLATAIGVRAAPYVDPLEAALVAQAEKYIPTIVHHTR    55

..LIGTFSYLLLKPLLRNSGLVDEKKGAYRTSMIWYNVLLALFSAL..........    64
                GFLVAVESPLARELPLMNPFHVLLIVLAYLVTVFVGMQIMKNFERFEVKTFSLLH    110

.......SFYVTATALGWDYGTGAWLRRQTGDTPQPLFQCPSPVWDSKLFTWTAK    112
                NFCLVSISAYMCGGILYEAYQANYGLFENAADHTFKGLPMAKMIWL.........    156

AFYYSKYVEYLDTAWLRV........SFLQAFHHFGAPWDVYLGIRLHNEGVWIFM    160
                .FYFSKIMEFVDTMIMVLKKNNRQISFLHVYHHSSIFTIWWLVTFVAPNGEAYFS    210

FF.NSFIHTIMYTYYGLTAAGYKFKA..KPLITAMQICQFVGGFLLVWDYINV.P    211
                AALNSFIHVIMYGYYFLSALGFKQVSFIKFYITRSQMTQFCMMSVQSSWDMYAMK    265

CFNSDKGKLFSWAFNYAYVGSVFLLFCHFFYQDN.LATKKSAKAGKQL......    258
                VLGRPGYPFFITALLWFYMWTMLGLFYNFYRKNAKLAKQAKADAAKEKARKLQ      318
```

Fig. 2  Pairwise alignment of of polypeptides of Ig_ASE1 (upper row) and mouse (lower row). Identities are shown in bold characters.

```
IgASE1         ............................MALANDAGERIWAAVTDPEILIGTFSY         27
Elovl4_(Mus)   MGLLDSEPGSVLNAMSTAFNDTVEFYRWTWTIADKRVADWPLMQSPWPTISISTL         55

LLLKPLLRNSGLIVDEKKGAYRTSMIWYN...VLLALFSALSFYVTATALGWDYGT         79
               YLLFVWLGPKWMKDREPFQMRLVLIIYNFGMVLLNLFIFRELFMGSYNAGYSYIC        110

GAWLRRQTGDTPQPLFQCPSPVWDSKLFTWTAKAFYYSKYVEYLDTAWLR......        129
               QSVDY.........SNDVNEVRIAAALMWYFVSKGVEYLDTVFFILRKKN             151

..VSFLQAFHHFGAPWDVYLGIRLHNEGVWIFMFF.NSFIHTIMYTYYGLTAAGY        181
               NQVSFLHVYHCTMFTLMWIGIKWVAGGQAPFGAQMNSFIHVIMYSYYGLTAFGP        206

KFKAKPLITAMQICQFVGGFLLVWDYINVPCFNSDKGKLFSWAFNYAYVGSVFLL        236
               WIQKYLWWKRYLTMLQLVQFHVTIGHTALSLYTDCPFPKWMHWALLAYAISFIFL        261

FCHFFYQDNLATKKSAKAGKQL................................        258
               FLNFYTRTYNEPKQS.KIGKTATNGISSNGVNKSEKALENGKPQKNGKPKGE           312
```

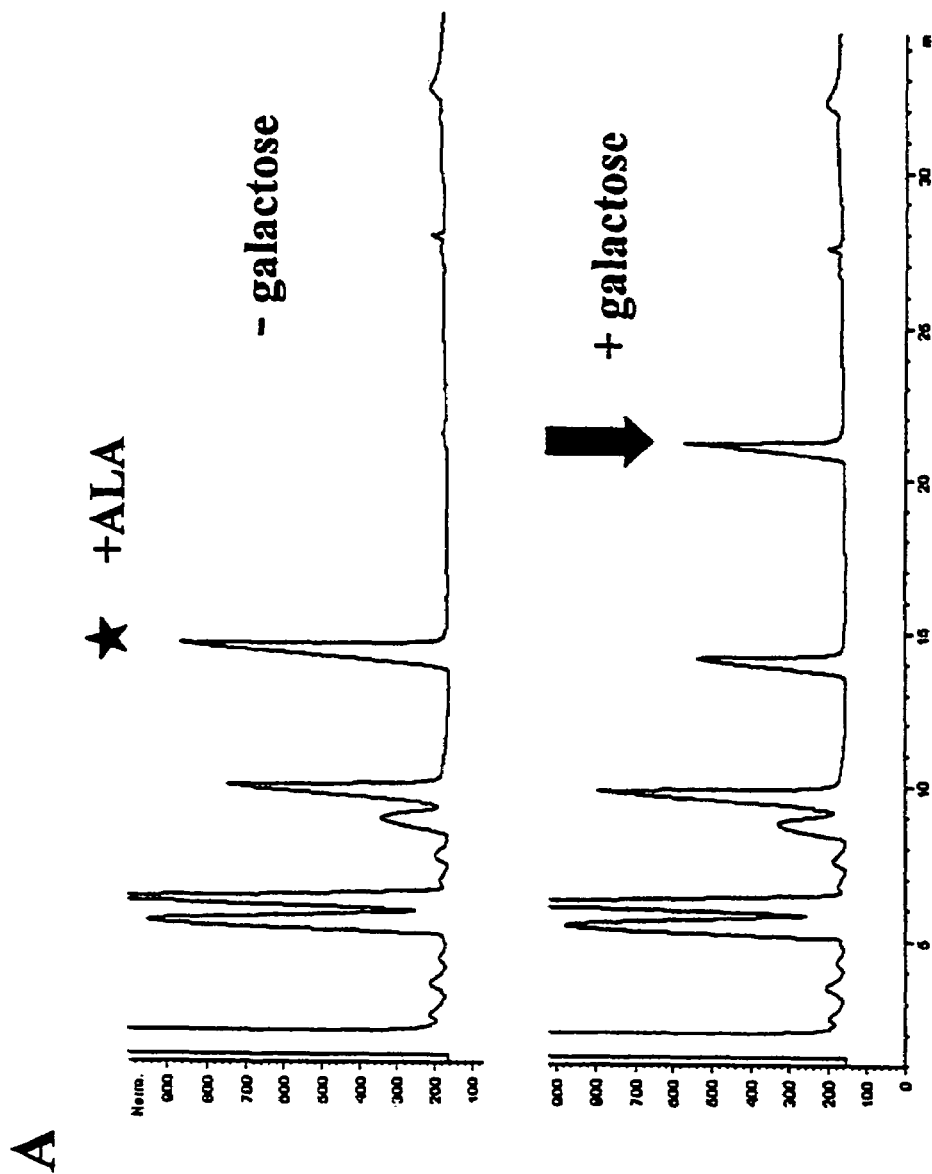
Figure 3 A-D: HPLC chromatograms of fatty acid methyl esters isolated from yeast expressing the Ig_ASE1 gene product

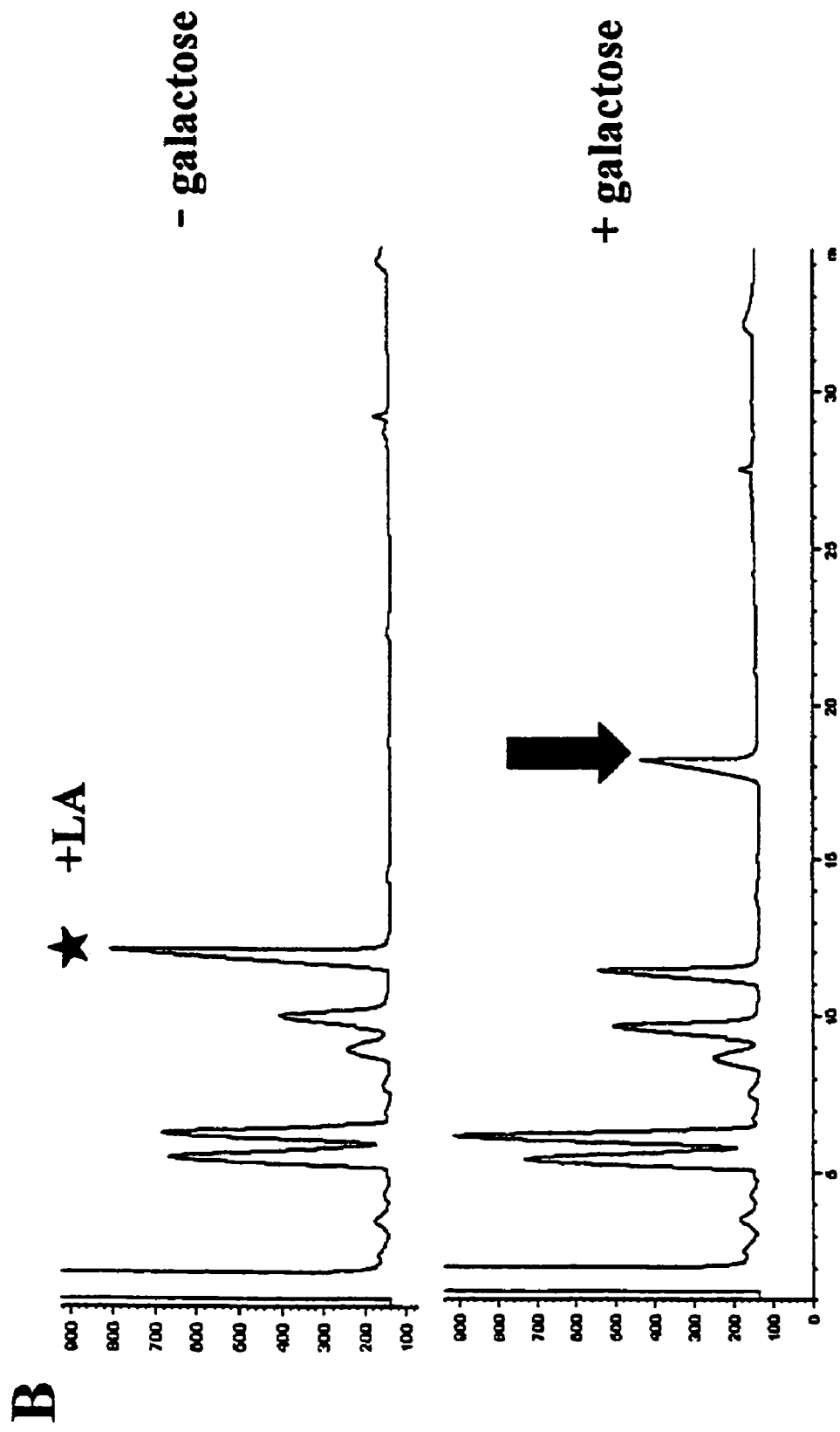
Figure 3 A-D: HPLC chromatograms of fatty acid methyl esters isolated from yeast expressing the Ig_ASE1 gene product

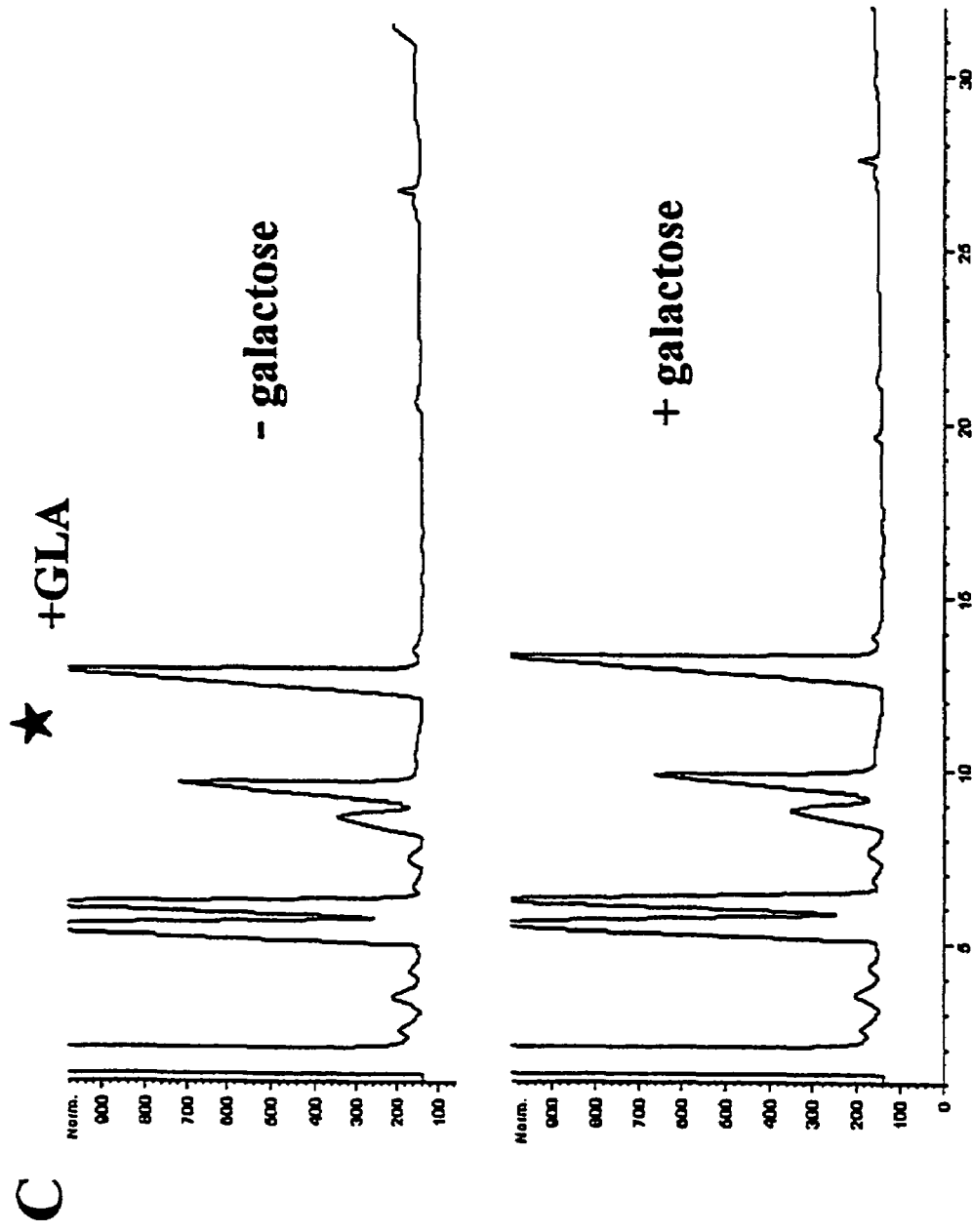
Figure 3 A-D: HPLC chromatograms of fatty acid methyl esters isolated from yeast expressing the Ig_ASB1 gene product

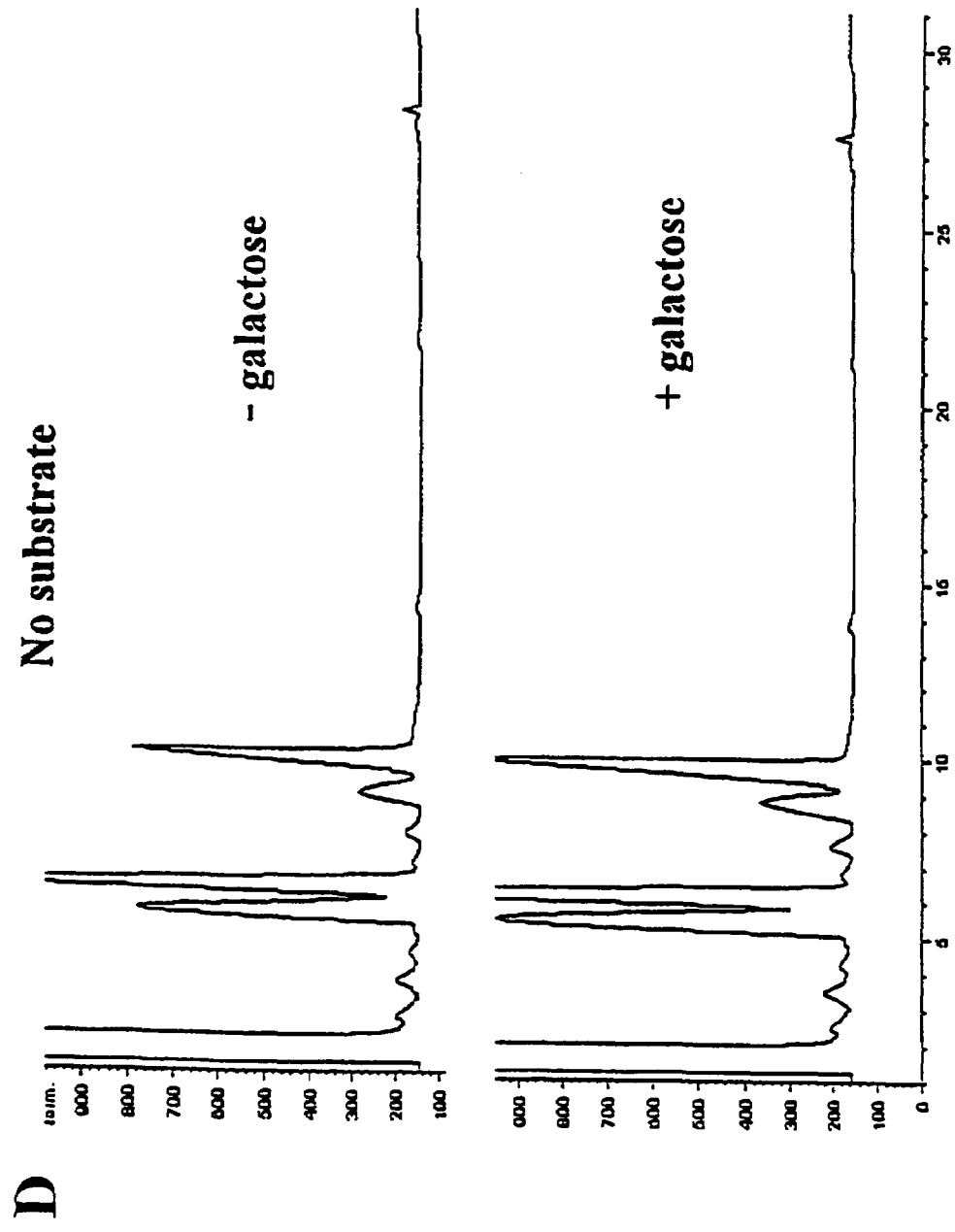
Figure 3 A-D: HPLC chromatograms of fatty acid methyl esters isolated from yeast expressing the Ig_ASE1 gene product

SEQUENCE LISTING

```
<160> NUMBER OF SEQ ID NOS: 15

<210> SEQ ID NO 1
<211> LENGTH: 1064
<212> TYPE: DNA
<213> ORGANISM: Isochrysis galbana
<220> FEATURE:
<221> NAME/KEY: CDS
<222> LOCATION: (2)..(790)

<400> SEQUENCE: 1 g atg gcc ctc gca aac gac gcg gga gag cgc atc tgg gcg gct gtg acc        49
  Met Ala Leu Ala Asn Asp Ala Gly Glu Arg Ile Trp Ala Ala Val Thr
    1               5                  10                  15 gac ccg gaa atc ctc att ggc acc ttc tcg tac ttg cta ctc aaa ccg          97
Asp Pro Glu Ile Leu Ile Gly Thr Phe Ser Tyr Leu Leu Leu Lys Pro
             20                  25                  30 ctg ctc cgc aat tcc ggg ctg gtg gat gag aag aag ggc gca tac agg         145
Leu Leu Arg Asn Ser Gly Leu Val Asp Glu Lys Lys Gly Ala Tyr Arg
         35                  40                  45 acg tcc atg atc tgg tac aac gtt ctg ctg gcg ctc ttc tct gcg ctg         193
Thr Ser Met Ile Trp Tyr Asn Val Leu Leu Ala Leu Phe Ser Ala Leu
     50                  55                  60 agc ttc tac gtg acg gcg acc gcc ctc ggc tgg gac tat ggt acg ggc         241
Ser Phe Tyr Val Thr Ala Thr Ala Leu Gly Trp Asp Tyr Gly Thr Gly
 65                  70                  75                  80 gcg tgg ctg cgc agg caa acc ggc gac aca ccg cag ccg ctc ttc cag         289
Ala Trp Leu Arg Arg Gln Thr Gly Asp Thr Pro Gln Pro Leu Phe Gln
                 85                  90                  95 tgc ccg tcc ccg gtt tgg gac tcg aag ctc ttc aca tgg acc gcc aag         337
Cys Pro Ser Pro Val Trp Asp Ser Lys Leu Phe Thr Trp Thr Ala Lys
            100                 105                 110 gca ttc tat tac tcc aag tac gtg gag tac ctc gac acg gcc tgg ctg         385
Ala Phe Tyr Tyr Ser Lys Tyr Val Glu Tyr Leu Asp Thr Ala Trp Leu
        115                 120                 125 gtg ctc aag ggc aag agg gtc tcc ttt ctc cag gcc ttc cac cac ttt         433
Val Leu Lys Gly Lys Arg Val Ser Phe Leu Gln Ala Phe His His Phe
```

```
            130                 135                 140
ggc gcg ccg tgg gat gtg tac ctc ggc att cgg ctg cac aac gag ggc      481
Gly Ala Pro Trp Asp Val Tyr Leu Gly Ile Arg Leu His Asn Glu Gly
145                 150                 155                 160 gta tgg atc ttc atg ttt ttc aac tcg ttc att cac acc atc atg tac      529
Val Trp Ile Phe Met Phe Phe Asn Ser Phe Ile His Thr Ile Met Tyr
                165                 170                 175 acc tac tac ggc ctc acc gcc gcc ggg tat aag ttc aag gcc aag ccg      577
Thr Tyr Tyr Gly Leu Thr Ala Ala Gly Tyr Lys Phe Lys Ala Lys Pro
            180                 185                 190 ctc atc acc gcg atg cag atc tgc cag ttc gtg ggc ggc ttc ctg ttg      625
Leu Ile Thr Ala Met Gln Ile Cys Gln Phe Val Gly Gly Phe Leu Leu
        195                 200                 205 gtc tgg gac tac atc aac gtc ccc tgc ttc aac tcg gac aaa ggg aag      673
Val Trp Asp Tyr Ile Asn Val Pro Cys Phe Asn Ser Asp Lys Gly Lys
    210                 215                 220 ttg ttc agc tgg gct ttc aac tat gca tac gtc ggc tcg gtc ttc ttg      721
Leu Phe Ser Trp Ala Phe Asn Tyr Ala Tyr Val Gly Ser Val Phe Leu
225                 230                 235                 240 ctc ttc tgc cac ttt ttc tac cag gac aac ttg gca acg aag aaa tcg      769
Leu Phe Cys His Phe Phe Tyr Gln Asp Asn Leu Ala Thr Lys Lys Ser
                245                 250                 255 gcc aag gcg ggc aag cag ctc taggcctcga gccggctcgc gggttcaagg         820
Ala Lys Ala Gly Lys Gln Leu
            260 agggcgacac gggggtggga cgtctgcatg gagatggatt gtggatgtcc ttacgcctta    880 ctcatcaatg tcctcccatc tctcccctct agaccttcta ctagccatct agaagggcag    940 ctcagagacg gataccgttc ccctcccct tcctttttcgt ctttgctttg ccattgtttg    1000 tttgtctcta ttttttaaac tattgacgct aacgcgttac gctcgcaaaa aaaaaaaaa    1060 aaaa                                                                 1064

<210> SEQ ID NO 2
<211> LENGTH: 263
<212> TYPE: PRT
<213> ORGANISM: Isochrysis galbana

<400> SEQUENCE: 2

Met Ala Leu Ala Asn Asp Ala Gly Glu Arg Ile Trp Ala Ala Val Thr
  1               5                  10                  15

Asp Pro Glu Ile Leu Ile Gly Thr Phe Ser Tyr Leu Leu Leu Lys Pro
                 20                  25                  30

Leu Leu Arg Asn Ser Gly Leu Val Asp Glu Lys Lys Gly Ala Tyr Arg
             35                  40                  45

Thr Ser Met Ile Trp Tyr Asn Val Leu Leu Ala Leu Phe Ser Ala Leu
         50                  55                  60

Ser Phe Tyr Val Thr Ala Thr Leu Gly Trp Asp Tyr Gly Thr Gly Gly
 65                  70                  75                  80

Ala Trp Leu Arg Arg Gln Thr Gly Asp Thr Pro Gln Pro Leu Phe Gln
                 85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Arg Val Ser Phe Leu Gln Ala Phe His His Phe
    130                 135                 140
```

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260

<210> SEQ ID NO 3
<211> LENGTH: 7
<212> TYPE: PRT
<213> ORGANISM: Artificial Sequence
<220> FEATURE:
<223> OTHER INFORMATION: common motif chosen for oligonucleotide design
<220> FEATURE:
<221> NAME/KEY: UNSURE
<222> LOCATION: 3
<223> OTHER INFORMATION: Xaa = unknown

<400> SEQUENCE: 3

Met Tyr Xaa Tyr Tyr Phe Leu
  1               5

<210> SEQ ID NO 4
<211> LENGTH: 20
<212> TYPE: DNA
<213> ORGANISM: Artificial Sequence
<220> FEATURE:
<223> OTHER INFORMATION: synthesized reverse complement oligo
<220> FEATURE:
<221> NAME/KEY: modified_base
<222> LOCATION: 12..14
<223> OTHER INFORMATION: n is inosine

<400> SEQUENCE: 4
aaaaaataat annngtacat                                           20

<210> SEQ ID NO 5
<211> LENGTH: 20
<212> TYPE: DNA
<213> ORGANISM: Artificial Sequence
<220> FEATURE:
<223> OTHER INFORMATION: synthesized reverse complement oligo
<220> FEATURE:
<221> NAME/KEY: modified_base
<222> LOCATION: 12..14
<223> OTHER INFORMATION: n is inosine

<400> SEQUENCE: 5
aggaagtagt annnatacat                                           20

<210> SEQ ID NO 6
<211> LENGTH: 20
<212> TYPE: DNA

```
<213> ORGANISM: Artificial Sequence
<220> FEATURE:
<223> OTHER INFORMATION: universal T3 promoter primer

<400> SEQUENCE: 6
aattaaccct cactaaaggg                                              20

<210> SEQ ID NO 7
<211> LENGTH: 20
<212> TYPE: DNA
<213> ORGANISM: Artificial Sequence
<220> FEATURE:
<223> OTHER INFORMATION: gene-specific sense primer

<400> SEQUENCE: 7
actcgaagct cttcacatgg                                              20

<210> SEQ ID NO 8
<211> LENGTH: 17
<212> TYPE: DNA
<213> ORGANISM: Artificial Sequence
<220> FEATURE:
<223> OTHER INFORMATION: universal M13 forward primer

<400> SEQUENCE: 8
gtaaaacgac ggccagt                                                 17

<210> SEQ ID NO 9
<211> LENGTH: 18
<212> TYPE: DNA
<213> ORGANISM: Artificial Sequence
<220> FEATURE:
<223> OTHER INFORMATION: sequencing primer

<400> SEQUENCE: 9
caggaaacag ctatgacc                                                18

<210> SEQ ID NO 10
<211> LENGTH: 19
<212> TYPE: DNA
<213> ORGANISM: Artificial Sequence
<220> FEATURE:
<223> OTHER INFORMATION: sequencing primer

<400> SEQUENCE: 10
ctaaagggaa caaaagctg                                               19

<210> SEQ ID NO 11
<211> LENGTH: 18
<212> TYPE: DNA
<213> ORGANISM: Artificial Sequence
<220> FEATURE:
<223> OTHER INFORMATION: sequencing primer

<400> SEQUENCE: 11
tgtaaaacga cggccagt                                                18

<210> SEQ ID NO 12
<211> LENGTH: 23
<212> TYPE: DNA
<213> ORGANISM: Artificial Sequence
<220> FEATURE:
<223> OTHER INFORMATION: forward primer

<400> SEQUENCE: 12
ggtaccatgg ccctcgcaaa cga                                          23
```

<210> SEQ ID NO 13
<211> LENGTH: 19
<212> TYPE: DNA
<213> ORGANISM: Artificial Sequence
<220> FEATURE:
<223> OTHER INFORMATION: reverse primer

<400> SEQUENCE: 13
taggacatcc acaatccat                                                  19

<210> SEQ ID NO 14
<211> LENGTH: 318
<212> TYPE: PRT
<213> ORGANISM: Mortierella alpina

<400> SEQUENCE: 14

Met Glu Ser Ile Ala Pro Phe Leu Pro Ser Lys Met Pro Gln Asp Leu
 1               5                  10                  15

Phe Met Asp Leu Ala Thr Ala Ile Gly Val Arg Ala Ala Pro Tyr Val
             20                  25                  30

Asp Pro Leu Glu Ala Ala Leu Val Ala Gln Ala Glu Lys Tyr Ile Pro
         35                  40                  45

Thr Ile Val His His Thr Arg Gly Phe Leu Val Ala Val Glu Ser Pro
     50                  55                  60

Leu Ala Arg Glu Leu Pro Leu Met Asn Pro Phe His Val Leu Leu Ile
 65                  70                  75                  80

Val Leu Ala Tyr Leu Val Thr Val Phe Val Gly Met Gln Ile Met Lys
                 85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ile Phe Pro
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315

<210> SEQ ID NO 15
<211> LENGTH: 312
<212> TYPE: PRT
<213> ORGANISM: Mouse

<400> SEQUENCE: 15

Met Gly Leu Leu Asp Ser Glu Pro Gly Ser Val Leu Asn Ala Met Ser
                5                   10                  15

Thr Ala Phe Asn Asp Thr Val Glu Phe Tyr Arg Trp Thr Trp Thr Ile
            20                  25                  30

Ala Asp Lys Arg Val Ala Asp Trp Pro Leu Met Gln Ser Pro Trp Pro
        35                  40                  45

Thr Ile Ser Ile Ser Thr Leu Tyr Leu Leu Phe Val Trp Leu Gly Pro
    50                  55                  60

Lys Trp Met Lys Asp Arg Glu Pro Phe Gln Met Arg Leu Val Leu Ile
65                  70                  75                  80

Ile Tyr Asn Phe Gly Met Val Leu Leu Asn Leu Phe Ile Phe Arg Glu
                85                  90                  95

Leu Phe Met Gly Ser Tyr Asn Ala Gly Tyr Ser Tyr Ile Cys Gln Ser
            100                 105                 110

Val Asp Tyr Ser Asn Asp Val Asn Glu Val Arg Ile Ala Ala Ala Leu
        115                 120                 125

Trp Trp Tyr Phe Val Ser Lys Gly Val Glu Tyr Leu Asp Thr Val Phe
    130                 135                 140

Phe Ile Leu Arg Lys Lys Asn Asn Gln Val Ser Phe Leu His Val Tyr
145                 150                 155                 160

His His Cys Thr Met Phe Thr Leu Trp Trp Ile Gly Ile Lys Trp Val
                165                 170                 175

Ala Gly Gly Gln Ala Phe Phe Gly Ala Gln Met Asn Ser Phe Ile His
            180                 185                 190

Val Ile Met Tyr Ser Tyr Tyr Gly Leu Thr Ala Phe Gly Pro Trp Ile
        195                 200                 205

Gln Lys Tyr Leu Trp Trp Lys Arg Tyr Leu Thr Met Leu Gln Leu Val
    210                 215                 220

Gln Phe His Val Thr Ile Gly His Thr Ala Leu Ser Leu Tyr Thr Asp
225                 230                 235                 240

Cys Pro Phe Pro Lys Trp Met His Trp Ala Leu Ile Ala Tyr Ala Ile
                245                 250                 255

Ser Phe Ile Phe Leu Phe Leu Asn Phe Tyr Thr Arg Thr Tyr Asn Glu
            260                 265                 270

Pro Lys Gln Ser Lys Thr Gly Lys Thr Ala Thr Asn Gly Ile Ser Ser
        275                 280                 285

Asn Gly Val Asn Lys Ser Glu Lys Ala Leu Glu Asn Gly Lys Pro Gln
    290                 295                 300

Lys Asn Gly Lys Pro Lys Gly Glu
305                 310

ELONGASE GENE AND PRODUCTION OF Δ9-POLYUNSATURATED FATTY ACIDS

FIELD OF THE INVENTION

This invention relates to a new elongase gene having the sequence SEQ ID NO: 1 or its derivatives, to a gene construct comprising this sequence or its derivatives and to its use. The inventive nucleic acid sequence encodes a polypeptide which elongates α-linolenic acid ($C_{18:3\ \Delta 9, 12, 15}$) by at least two carbon atoms whereas γ-linolenic acid ($C_{18:3\ \Delta 6, 9, 12}$) is not elongated. The invention additionally relates to vectors or organisms comprising an elongase gene having the sequence SEQ ID NO: 1 or its derivatives.

The invention further relates to a process for the production of polyunsaturated fatty acids (=PUFAs) with an organism which comprises the elongase gene and which organism produces high amounts of oils and especially oils with a high content of unsaturated fatty acids. Additionally the invention relates to an oil and/or fatty acid composition with a higher content of polyunsaturated $C_{20}$- or $C_{22}$-fatty acids with at least two double bonds and/or to a triacylglycerol composition with a higher content of said polyunsaturated fatty acids.

BACKGROUND OF THE INVENTION

Certain products and by-products of naturally-occurring metabolic processes in cells have utility in a wide array of industries, including the food, feed, cosmetics, and pharmaceutical industries. These molecules, collectively termed 'fine chemicals', also include lipids and fatty acids whereof one representative class of molecules is polyunsaturated fatty acids. Polyunsaturated fatty acids (=PUFAs) are added for example to infant formulas to create a higher nutrition value of such formulas. PUFAs have for example a positive influence on the cholesterol level of the blood in humans and therefore are useful in the protection against heart diseases. Fine chemicals and polyunsaturated fatty acids (=PUFAs) can be isolated from animal sources such as for example fish or produced with microorganisms through the large-scale fermentation of microorganisms developed to produce and accumulate or secrete large quantities of one or more desired molecules.

Particularly useful microorganisms for the production of PUFAs are microorganisms such as the algae *Isochrysis galbana*, *Phaedactylum tricornutum* or *Crypthecodinium* species, ciliates like *Stylonychia* or *Colpidium*, fungi like *Mortierella*, *Entomophthora*, *Mucor* or *Thrausto-/Schizochytrium* species. Through strain selection, a number of mutant strains of the respective microorganisms have been developed which produce an array of desirable compounds including PUFAs. However, selection of strains improved for the production of a particular molecule is a time-consuming and difficult process.

Alternatively the production of fine chemicals can be most conveniently performed via the large scale production of plants developed to produce aforementioned PUFAs. Particularly well suited plants for this purpose are oilseed plants containing high amounts of lipid compounds such as rapeseed, canola, linseed, soybean, sunflower, borage and evening primrose. But also other crop plants containing oils or lipids and fatty acids are well suited as mentioned in the detailed description of this invention. Through conventional breeding, a number of mutant plants have been developed which produce an array of desirable lipids and fatty acids, cofactors and enzymes. However, selection of new plant cultivars bred for the production of a particular molecule is a time-consuming and difficult process or even impossible if the compound does not naturally occur in the respective oil crop as in the case of $C_{20}$ and higher carbon chain polyunsaturated fatty acids.

SUMMARY OF THE INVENTION

This invention provides a novel nucleic acid molecule as described in SEQ ID NO: 1 which may be used to modify oils, fatty acids, lipids, lipid derived compounds and most preferred to produce polyunsaturated fatty acids.

Microorganisms such as *Mortierella*, *Entomophthora*, *Mucor*, *Crypthecodinium* as well as other algae and fungi and plants, especially oilseed plants, are commonly used in industry for the large-scale production of a variety of fine chemicals.

Given the availability of cloning vectors and techniques for genetic manipulation of the abovementioned microorganisms and ciliates such as disclosed in WO 98/01572 or algae and related organisms such as *Phaeodactylum tricornutum* described in Falciatore et al., 1999, Marine Biotechnology 1 (3):239-251 as well as Dunahay et al. 1995, Genetic transformation of diatoms, J. Phycol. 31:10004-1012 and references therein, the nucleic acid molecules of the invention may be utilized in the genetic engineering of these organisms to make them better or more efficient producers of one or more fine chemicals. This improved production or efficiency of production of a fine chemical may be due to a direct effect of manipulation of a gene of the invention, or it may be due to an indirect effect of such manipulation.

Mosses and algae are the only known plant systems that produce considerable amounts of polyunsaturated fatty acids like arachidonic acid (ARA) and/or eicosapentaenoic acid (EPA) and/or docosahexaenoic acid (DHA). Therefore nucleic acid molecules originating from an alga like *Isochrysis galbana* are especially suited to modify the lipid and PUFA production system in a host, especially in microorganisms such as the abovementioned microorganisms and plants such as oilseed plants, for example rapeseed, canola, linseed, soybean, sunflower, borage. Furthermore nucleic acids from the alga *Isochrysis galbana* can be used to identify those DNA sequences and enzymes in other species which are useful to modify the biosynthesis of precursor molecules of PUFAs in the respective organisms.

The alga *Isochrysis galbana* shares a high degree of homology on the DNA sequence and polypeptide levels with other algae allowing the use of heterologous screening of DNA molecules with probes evolving from other algae or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference sequences for the mapping of other algae or for the derivation of PCR primers.

These novel nucleic acid molecules can encode proteins referred to herein as PUFA specific elongases (PSEs or singular PSE). These PSEs are capable of, for example, performing a function involved in the metabolism (e.g., the biosynthesis or degradation) of compounds necessary for lipid or fatty acid biosynthesis like PUFAs, or of assisting in the transmembrane transport of one or more lipid/fatty acid compounds either into or out of the cell.

In the present application we show the function of one of these sequences in more detail. We have isolated for the first time a functionally active gene encoding a highly specific elongase activity suitable to produce long chain unsaturated fatty acids from α-linolenic acid ($C_{18:3\ \Delta9, 12, 15}$) while γ-linolenic acid ($C_{18:3\ \Delta6, 9, 12}$) is not elongated. We will herein therefore refer to an ASE ("alpha-linolenic acid specific elongase") gene or protein thus representing an enzymatic activity leading to the elongation of omega-3 fatty acids or delta-9 desaturated long chain polyunsaturated fatty acids at least by two carbon atoms. Other publications and patents have not been able before to show a functionally active ASE gene that is specific for α-linolenic acid (ALA) and which does not accept γ-linolenic acid (GLA) as a substrate though there are various patent applications known showing the elongation of short or medium chain saturated fatty acids (WO 98/46776 and U.S. Pat. No. 5,475,099). WO 00/12720 describes various PSEs from various organisms but none of the described genes was shown to be specific for ALA while discriminating against GLA. Genes shown to encode PSEs from WO 00/12720 all accept GLA as a substrate, hence these enzymes lead to the elongation of Δ6 desaturated long chain polyunsaturated fatty acids but not of Δ9 desaturated fatty acids as disclosed in the present invention.

The unique feature of the ASE disclosed in the present invention is important as resulting products are limited to desired products while being free of unwanted PUFA molecules such as those resulting from the elongation of GLA.

WO 99/64616, WO 98/46763, WO 98/46764, WO 98/46765 describe the production of PUFAs in transgenic plants showing the cloning and functional expression of respective Δ12-, Δ5- or Δ6-desaturase activities from several sources lacking the demonstration of an ASE encoding gene or an α-linolenic acid specific Δ6-desaturase gene and functional activity necessary for the production of eicosapentaenoic acid and related precursors from ALA.

For the production of PUFAs it is necessary that the polyunsaturated fatty acid molecules such as the preferred $C_{18}$ fatty acids are elongated by at least two carbon atoms by the enzymatic activity of an elongase. The nucleic acid sequence of the invention encodes the first elongase derived from a plant which has the ability to elongate $C_{18:3\ \Delta6, 9, 12}$ fatty acids with at least two double bonds, preferably three double bonds, in the fatty acid by at least two carbon atoms. After one round of elongation this enzymatic activity leads to $C_{20}$ fatty acids and after two, three and four rounds of elongation to $C_{22}$, $C_{24}$ or $C_{26}$ fatty acids. With the elongase of the invention it is also possible to synthesize longer PUFAs. The activity of the elongase of the invention leads preferably to $C_{20}$ and/or $C_{22}$ fatty acids with at least two double bonds in the fatty acid molecule, preferably with three or four double bonds, particularly preferably three double bonds, in the fatty acid molecule. Preferred fatty acid molecules of the elongation are fatty acid molecules with a double bond in Δ9-postion. After the elongation with the inventive enzyme has taken place further desaturation steps might occur. Therefore the products of the elongase activity and the possible further desaturation lead to preferred PUFAs with a higher desaturation grade such as docosadienoic acid, arachidonic acid, ω6-eicosatrienoic acid, dihomo-γ-linolenic acid, eicosapentenoic acid, ω3-eicosatrienoic acid, ω3-eicosatetraenoic acid, docosapentaenoic acid or docosahexaenoic acid. A particularly preferred fatty acid is the elongation product stearidonic acid of the α-linolenic acid ($C_{18:3\ \Delta9, 12, 15}$). Substrates of the enzymatic activity of the invention are preferably Δ9 desaturated fatty acids which have the first double bond in Δ9-postion such as axillarenic acid, vernolic acid ($C_{18}$, $\Delta9_{cis}$, 12-13$_{epoxy}$), conjugated linoleic acid ($C_{18}$, $\Delta9_{cis}$, 11$_{trans}$), sterolic acid ($C_{18}$, Δ9-acetylenic), α-parinaric acid ($C_{18}$, $\Delta9_{cis}$, 11$_{trans}$, 13$_{trans}$), palmitoleic acid ($C_{18}$, Δ9cis), linoleic acid or α-linolenic acid. Preferred substrates are linoleic acid and/or α-linolenic acid. The fatty acids with at least two double bonds in the fatty acid can be elongated by the enzymatic activity of the invention in the form of the free fatty acids, the acyl-CoA-fatty acids, alkyl esters of the fatty acids or in the form of the esters such as phospholipids, glycolipids, sphingolipids, phosphoglycerides, monoacylglycerides, diacylglycerides or triacylglycerides, preferably in the form of free fatty acid or the acyl-CoA-fatty acids.

Given the availability of cloning vectors for use in plants and plant transformation, such as those published in and cited therein: Plant Molecular Biology and Biotechnology (CRC Press, Boca Raton, Fla.), chapter 6/7, p. 71-119 (1993); F. F. White, Vectors for Gene Transfer in Higher Plants; in: Transgenic Plants, Vol. 1, Engineering and Utilization, eds.: Kung and R. Wu, Academic Press, 1993, 15-38; B. Jenes et al., Techniques for Gene Transfer, in: Transgenic Plants, Vol. 1, Engineering and Utilization, eds.: Kung and R. Wu, Academic Press (1993), 128-143; Potrykus, Annu. Rev. Plant Physiol. Plant Molec. Biol. 42 (1991), 205-225)), the nucleic acid molecules of the invention may be utilized in the genetic engineering of a wide variety of plants to make them better or more efficient producers of one or more lipid derived products such as PUFAs. This improved production or efficiency of production of a lipid derived product such as PUFAs may be due to a direct effect of manipulation of a gene of the invention, or it may be due to an indirect effect of such manipulation.

There are a number of mechanisms by which the alteration of an ASE protein of the invention may directly affect the yield, production, and/or efficiency of production of a fine chemical from an oilseed plant or microorganism due to such an altered protein. The ASE protein or gene may be increased in number or activity such that greater quantities of these compounds are produced or the compound may be produced de novo as the organisms were lacking this activity and capacity of biosynthesis before the introduction of the respective gene.

The introduction of an ASE gene into an organism or cell may not just increase the biosynthetic flux into an end product, it may also increase or create de novo the respective triacylglycerol composition. Similarly, other genes involved in the import of nutrients necessary for the biosynthesis of one or more fine chemicals (e.g., fatty acids, polar and neutral lipids) may be increased in number or activity such that these precursors, cofactors, or intermediate compounds are increased in concentration within the cell or within the storing compartment, thus increasing further the capability of the cell to produce PUFAs as described below. Fatty acids and lipids themselves are desirable fine chemicals; by optimizing the activity or increasing the number of one or more ASEs which participate in the biosynthesis of these compounds, or by impairing the activity of one or more ASEs which are involved in the degradation of these compounds, it may be possible to increase the yield, production, and/or efficiency of production of fatty acid and lipid molecules from plants or microorganisms.

The mutagenesis of the ASE gene of the invention may also result in an ASE protein having altered activities which directly or indirectly impact the production of one or more desired fine chemicals. For example the ASE gene of the invention may be increased in number or activity such that the normal metabolic wastes or byproducts of the cell (possibly increased in quantity due to the overproduction of the desired fine chemical) are efficiently exported before they are able to destroy other molecules or processes within the cell (which would decrease the viability of the cell) or to interfere with fine chemical biosynthetic pathways (which would decrease the yield, production, or efficiency of production of the desired fine chemical). Further, the relatively large intracellular quantities of the desired fine chemical may in themselves be toxic to the cell or may interfere with enzyme feedback mechanisms such as allosteric regulation; for example, by increasing the activity or number of other downstream enzymes or detoxifying enzymes of the PUFA pathway, it might increase the allocation of the PUFA into the triacylglycerol fraction, one might increase the viability of seed cells, in turn leading to a better development of cells in the culture or in a seed producing the desired fine chemical. The ASE gene of the invention may also be manipulated such that the relative amounts of different lipid and fatty acid molecules are produced. This may have a profound effect on the lipid composition of the membrane of the cell and would create novel oils in addition to the occurrence of newly synthesized PUFAs. Since each type of lipid has different physical properties, an alteration in the lipid composition of a membrane may significantly alter membrane fluidity. Changes in membrane fluidity can impact the transport of molecules across the membrane, as well as the integrity of the cell, both of which have a profound effect on the production of fine chemicals. In plants these changes can moreover also influence other characteristics like tolerance towards abiotic and biotic stress conditions.

Biotic and abiotic stress tolerance is a general trait desired to be inherited into a wide variety of plants like maize, wheat, rye, oats, triticale, rice, barley, soybean, peanut, cotton, rapeseed and canola, manihot, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut) and perennial grasses and forage crops. These crop plants are also preferred target plants for genetic engineering as one further embodiment of the present invention. Particularly preferred plants of the invention are oilseed plants such as soybean, peanut, rapeseed, canola, sunflower, safflower, trees (oil palm, coconut) or crops such as maize, wheat, rye, oats, triticale, rice, barley, alfalfa or bushy plants (coffee, cacao, tea).

In another embodiment, the isolated nucleic acid molecule encodes a protein or portion thereof wherein the protein or portion thereof includes an amino acid sequence which is sufficiently homologous to an amino acid sequence of sequence SEQ ID NO: 2 such that the protein or portion thereof maintains an ASE activity. Preferably, the protein or portion thereof encoded by the nucleic acid molecule maintains the ability to participate in the metabolism of compounds necessary for the construction of PUFAs or cellular membranes of plants or in the transport of molecules across these membranes. In one embodiment, the protein encoded by the nucleic acid molecule is at least about 50%, preferably at least about 60%, and more preferably at least about 70%, 80%, or 90% and most preferably at least about 95%, 96%, 97%, 98%, or 99% or more homologous to an amino acid sequence of sequence SEQ ID NO: 2. In another preferred embodiment, the protein is a full length *Isochrysis galbana* protein which is substantially homologous to an entire amino acid sequence of SEQ ID NO: 2 (derived from an open reading frame shown in SEQ ID NO: 1).

Accordingly, one aspect of the invention pertains to isolated nucleic acid molecules (e.g., cDNAs) comprising a nucleotide sequence encoding an ASE protein or biologically active portions thereof, as well as nucleic acid fragments suitable as primers or hybridization probes for the detection or amplification of ASE-encoding nucleic acids (e.g., DNA or mRNA). In particularly preferred embodiments, the nucleic acid molecule comprises one of the nucleotide sequences set forth in SEQ ID NO: 1, derivatives of said sequence or the coding region or a complement or enzymatically active part thereof. In other particularly preferred embodiments, the isolated nucleic acid molecule of the invention comprises a nucleotide sequence which hybridizes to or is at least about 50%, preferably at least about 60%, more preferably at least about 70%, 80% or 90%, and even more preferably at least about 95%, 96%, 97%, 98%, 99% or more homologous to a nucleotide sequence as in SEQ ID NO: 1, derivatives or a portion thereof. In other preferred embodiments, the isolated nucleic acid molecule encodes an amino acid sequence as set forth in SEQ ID NO: 2. The preferred ASE gene of the present invention also preferably possesses at least one of the ASE activities described herein.

In another preferred embodiment, the isolated nucleic acid molecule is derived from *Isochrysis galbana* and encodes a protein (e.g., an ASE fusion protein) which includes a biologically active domain which is at least about 50% or more homologous to one of the amino acid sequences of SEQ ID NO: 2 and is able to participate in the metabolism of compounds necessary for the construction of cellular membranes or in the transport of molecules across these membranes, or has one or more of the activities set forth in Tab. 2, and which also includes heterologous nucleic acid sequences encoding a heterologous polypeptide or regulatory regions.

In another embodiment, the isolated nucleic acid molecule is at least 15 nucleotides in length and hybridizes under stringent conditions with a nucleic acid molecule comprising a nucleotide sequence of SEQ ID NO: 1. Preferably, the isolated nucleic acid molecule corresponds to a naturally-occurring nucleic acid molecule. More preferably, the isolated nucleic acid encodes a naturally-occurring *Isochrysis galbana* ASE, or a biologically active portion thereof.

Another aspect of the invention pertains to vectors, e.g., recombinant expression vectors, containing the nucleic acid molecules of the invention, and host cells into which such vectors have been introduced, especially microorganisms, plant cells, plant tissue, plant organs or whole plants. In one embodiment, such a host cell is a cell capable of storing fine chemical compounds, especially PUFAs, in order to isolate the desired compound from harvested material. The compound (oils, lipids, triacyl glycerides, fatty acids) or the ASE can then be isolated from the medium or the host cell, which in plants are cells containing and storing fine chemical compounds, most preferably cells of storage tissues like seed coats, tubers, epidermal and seed cells.

Yet another aspect of the invention pertains to an isolated ASE gene shown in SEQ ID NO: 1 or a portion thereof, e.g., a biologically active portion thereof. In a preferred embodiment, the isolated ASE or portion thereof can participate in the metabolism of compounds necessary for the construction of cellular membranes in a microorganism or a plant cell, or in the transport of molecules across its membranes. In another preferred embodiment, the isolated ASE or portion thereof is sufficiently homologous to an amino acid sequence of SEQ ID NO: 2 such that the protein or portion thereof maintains the ability to participate in the metabolism of compounds necessary for the construction of cellular membranes in microorganisms or plant cells, or in the transport of molecules across these membranes.

Hence in another preferred embodiment, the alga *Isochrysis galbana* can be used to show the function of a moss gene using homologous recombination based on the nucleic acids-described in this invention.

Still another aspect of the invention pertains to an isolated ASE gene or a portion, e.g., a biologically active portion, thereof. In a preferred embodiment, the isolated ASE or portion thereof can participate in the metabolism of compounds necessary for the construction of cellular membranes in a microorganism or a plant cell, or in the transport of molecules across its membranes. In another preferred embodiment, the isolated PSE or portion thereof is sufficiently homologous to an amino acid sequence of SEQ ID NO: 2 such that the protein or portion thereof maintains the ability to participate in the metabolism of compounds necessary for the construction of cellular membranes in microorganisms or plant cells, or in the transport of molecules across these membranes.

The invention also provides an isolated preparation of an ASE. In preferred embodiments, the ASE gene comprises an amino acid sequence of SEQ ID NO: 2. In another preferred embodiment, the invention pertains to an isolated full length protein which is substantially homologous to an entire amino acid sequence of SEQ ID NO: 2 (encoded by an open reading frame set forth in SEQ ID NO: 1). In another embodiment, the protein is at least about 50%, preferably at least about 60%, and more preferably at least about 70%, 80%, or 90%, and most preferably at least about 95%, 96%, 97%, 98%, or 99% or more homologous to an entire amino acid sequence of SEQ ID NO: 2. In other embodiments, the isolated ASE comprises an amino acid sequence which is at least about 50% or more homologous to one of the amino acid sequences of SEQ ID NO: 2 and is able to participate in the metabolism of compounds necessary for the construction of fatty acids in a microorganism or a plant cell, or in the transport of molecules across these membranes, or has one or more of the PUFA elongating activities, thus meaning the elongation of C18 carbon chains being desaturated bearing at least two double bond positions.

Alternatively, the isolated ASE can comprise an amino acid sequence which is encoded by a nucleotide sequence which hybridizes, e.g., hybridizes under stringent conditions, or is at least about 50%, preferably at least about 60%, more preferably at least about 70%, 80%, or 90%, and even more preferably at least about 95%, 96%, 97%, 98%, or 99% or more homologous, to a nucleotide sequence of SEQUENCE ID NO: 1. It is also preferred that the preferred forms of ASEs also have one or more of the ASE activities described herein.

The ASE polypeptide, or a biologically active portion thereof, can be operatively linked to a non-ASE polypeptide to form a fusion protein. In preferred embodiments, this fusion protein has an activity which differs from that of the ASE alone. In other preferred embodiments, this fusion protein participates in the metabolism of compounds necessary for the synthesis of lipids and fatty acids, cofactors and enzymes in microorganisms or plants, or in the transport of molecules across the membranes of plants. In particularly preferred embodiments, integration of this fusion protein into a host cell modulates production of a desired compound from the cell. In a preferred embodiment such fusion proteins also contain Δ4-, Δ5- or Δ8-desaturase activities alone or in combination. Especially a Δ8-desaturase from *Euglena gracilis* described in WO 00/34439 and a Δ5-desaturase gene described in U.S. Pat. No. 6,051,754 (*M. alpina*), GB9814034.6 (*C. elegans*) or a Δ12- and Δ15-desaturase gene described in U.S. Pat. No. 5,850,026 are suitable genes for coexpression with an ASE gene of the present invention. None of the cited patents shows coexpression with an ASE gene described in the present invention.

Another aspect of the invention pertains to a method for producing a fine chemical. This method involves either the culturing of a suitable microorganism or culturing plant cells, tissues, organs or whole plants containing a vector directing the expression of an ASE nucleic acid molecule of the invention, such that a fine chemical is produced. In a preferred embodiment, this method further includes the step of obtaining a cell containing such a vector, in which a cell is transformed with a vector directing the expression of an ASE nucleic acid. In another preferred embodiment, this method includes the step of recovering the fine chemical from the culture. In a particularly preferred embodiment, the cell is from an alga such as *Phaeodactylum*, ciliates such as *Colpidium* or *Stylonichia*, fungi such as *Mortierella* or *Thraustochytrium* or *Schizochytrium* or from oilseed plants as mentioned above.

Another aspect of the invention pertains to methods for modulating production of a molecule from a microorganism. Such methods include contacting the cell with an agent which modulates ASE activity or ASE nucleic acid expression such that a cell associated activity is altered relative to this same activity in the absence of the agent. In a preferred embodiment, the cell is modulated for one or more metabolic pathways for lipids and fatty acids, cofactors and enzymes or is modulated for the transport of compounds across such membranes, such that the yields or rates of production of a desired fine chemical by this microorganism are improved. The agent which modulates ASE activity can be an agent which stimulates ASE activity or ASE nucleic acid expression. Examples of agents which stimulate ASE activity or ASE nucleic acid expression include small molecules, active ASEs, and nucleic acids encoding ASEs that have been introduced into the cell. Examples of agents which inhibit ASE activity or expression include small molecules and antisense ASE nucleic acid molecules.

Another aspect of the invention pertains to methods for modulating yields of a desired compound from a cell, involving the introduction of a wild-type or mutant ASE gene into a cell, the gene being either maintained on a separate plasmid or integrated into the genome of the host cell. If integrated into the genome, such integration can be random, or it can take place by recombination such that the native gene is replaced by the introduced copy, causing the production of the desired compound from the cell to be modulated or by using a gene in trans such that the gene is functionally linked to a functional expression unit containing at least a sequence facilitating the expression of a gene and a sequence facilitating the polyadenylation of a functionally transcribed gene.

In a preferred embodiment, said yields are modified. In another preferred embodiment, said desired chemical is increased while unwanted disturbing compounds can be decreased. In a particularly preferred-embodiment, said desired fine chemical is a lipid or fatty acid, cofactor or enzyme. In an especially preferred embodiment, said chemical is a polyunsaturated fatty acid. More preferably it is chosen from arachidonic acid (ARA), eicosapentaenoic acid (EPA) or docosahexaenoic acid (DHA).

BRIEF DESCRIPTION OF THE DRAWINGS

FIG. 1: shows the pairwise alignment of *Isochrysis galbana* elongase (Ig_ASE1, upper row) with *Mortierella alpina* elongase (SEQ ID NO:14) (M.AlpinaGlelo. lower row). Identities are shown in bold characters.

FIG. 2: shows the pairwise alignment of polypeptides of Ig_ASE1 (upper row) and mouse (SEQ ID NO:15) (lower row). Identities are shown in bold characters.

FIGS. 3A-3D illustrate HPLC chromatograms of fatty acid methyl esters isolated from yeast expressing the Ig_ASE1 gene product.

DETAILED DESCRIPTION OF THE INVENTION

The present invention provides ASE nucleic acid and protein molecules which are involved in the metabolism of lipids and fatty acids, PUFA cofactors and enzymes in the alga *Isochrysis galbana* or in the transport of lipophilic compounds across membranes. The molecules of the invention may be utilized in the modulation of production of fine chemicals from microorganisms, such as ciliates such as *Colpidium* or *Stylonichia*, fungi such as *Mortierella* or *Thraustochytrium* or *Schizochytrium*, algae such as *Phaeodactylum*, and/or plants like maize, wheat, rye, oats, triticale, rice, barley, soybean, peanut, cotton, *Brassica* species like rapeseed, canola and turnip rape, linseed, pepper, sunflower, borage, evening primrose and tagetes, solanaceous plants like potato, tobacco, eggplant, and tomato, *Vicia* species, pea, manihot, alfalfa, bushy plants (coffee, cacao, tea), *Salix* species, trees (oil palm, coconut) and perennial grasses and forage crops either directly (e.g., where overexpression or optimization of a fatty acid biosynthesis protein has a direct impact on the yield, production, and/or efficiency of production of the fatty acid from modified organisms), or may have an indirect impact which nonetheless results in an increase of yield, production, and/or efficiency of production of a desired compound or decrease of undesired compounds (e.g., where modulation of the metabolism of lipids and fatty acids, cofactors and enzymes results in alterations in the yield, production, and/or efficiency of production or the composition of desired compounds within the cells, which in turn may impact the production of one or more fine chemicals). Aspects of the invention are further explicated below.

I. Fine Chemicals and PUFAs

The term 'fine chemical' is art-recognized and includes molecules produced by an organism which have applications in various industries, such as, but not limited to, the pharmaceutical, agriculture, food, feed and cosmetics industries. Such compounds also include lipids, fatty acids, cofactors and enzymes etc. (as described e.g. in Kuninaka, A. (1996) Nucleotides and related compounds, p. 561-612, in Biotechnology vol. 6, Rehm et al., eds. VCH: Weinheim, and references contained therein), lipids, both saturated and polyunsaturated fatty acids (e.g., arachidonic acid), vitamins and cofactors (as described in Ullmann's Encyclopedia of Industrial Chemistry, vol. A27, Vitamins, p. 443-613 (1996) VCH Weinheim and references therein; and Ong, A. S., Niki, E. & Packer, L. (1995) Nutrition, Lipids, Health, and Disease Proceedings of the UNESCO/Confederation of Scientific and Technological Associations in Malaysia, and the Society for Free Radical Research, Asia, held Sep. 1-3, 1994 at Penang, Malaysia, AOCS Press, (1995)), enzymes, and all other chemicals described by Gutcho (1983) in Chemicals by Fermentation, Noyes Data Corporation, ISBN: 0818805086 and references therein. The metabolism and uses of certain of these fine chemicals are further explicated below.

The combination of various precursor molecules and biosynthetic enzymes results in the production of different fatty acid molecules, which has a profound effect on the composition of the membrane. It can be assumed that PUFAs will not just be incorporated into triacylglycerol but also into membrane lipids.

The synthesis of membranes is a well-characterized process involving a number of components including lipids as part of the bilayer membrane. The production of new fatty acids such as PUFAs may therefore create new characteristics of membrane functions within a cell or organism.

Cellular membranes serve a variety of functions in a cell. First and foremost, a membrane differentiates the contents of a cell from the surrounding environment, thus giving integrity to the cell. Membranes may also serve as barriers to the influx of hazardous or unwanted compounds, and also to the efflux of desired compounds.

For more detailed descriptions and implications of membranes and involved mechanisms see: Bamberg, E. et al., (1993) Charge transport of ion pumps on lipid bilayer membranes, Q. Rev. Biophys. 26: 1-25; Gennis, R. B. (1989) Pores, Channels and Transporters, in: Biomembranes, Molecular Structure and Function, Springer: Heidelberg, p. 270-322; and Nikaido, H. and Saier, H. (1992) Transport proteins in bacteria: common themes in their design, Science 258: 936-942, and references contained within each of these references.

Lipid synthesis may be divided into two parts: the synthesis of fatty acids and their attachment to sn-glycerol-3-phosphate, and the addition or modification of a polar head group. Typical lipids utilized in membranes include phospholipids, glycolipids, sphingolipids, and phosphoglycerides. Fatty acid synthesis begins with the conversion of acetyl CoA either to malonyl CoA by acetyl CoA carboxylase, or to acetyl-ACP by acetyltransacylase. Following a condensation reaction, these two product molecules together form further intermediates, which are converted by a series of condensation, reduction and dehydration reactions to yield a saturated fatty acid molecule having the desired chain length. The production of unsaturated fatty acids from such molecules is catalyzed by specific desaturases either aerobically, with the help of molecular oxygen, or anaerobically (for reference on fatty acid synthesis in microorganisms, see F. C. Neidhardt et al. (1996) *E. coli* and *Salmonella*. ASM Press: Washington, D.C., p. 612-636 and references contained therein; Lengeler et al. (eds) (1999) Biology of Procaryotes. Thieme: Stuttgart, N.Y., and references contained therein; and Magnuson, K. et al., (1993) Microbiological Reviews 57: 522-542, and references contained therein).

Preferred precursors for the inventive PUFA biosynthesis process are linoleic and linolenic acid. These $C_{18}$ carbon fatty acids have to be elongated to $C_{20}$ and $C_{22}$ in order to obtain eicosa and docosa chain type fatty acids. With the aid of various desaturases such as enzymes with $\Delta 6$- or $\Delta 8$- and $\Delta 5$- and $\Delta 4$-desaturases activity eicosapentaenoic acid and docosahexaenoic acid as well as various other long chain PUFAs can be obtained, extracted and used for various purposes, for example in food and feed applications.

For the production of long chain PUFAs it is necessary as mentioned above that the polyunsaturated $C_{18}$ fatty acids are elongated by at least two carbon atoms by the enzymatic activity of the inventive elongase. The nucleic acid sequence of the invention encodes the first plant elongase which has the ability to elongate α-linolenic acid ($C_{18:3\ d9,\ 12,\ 15}$) by at least two carbon atoms but not γ-linolenic acid ($C_{18:3\ d6,\ 9,\ 12}$).

Furthermore fatty acids have to be transported and incorporated into the triacylglycerol storage lipid subsequent to various modifications. Another essential step in lipid synthesis is the transfer of fatty acids onto the polar head groups by, for example, glycerol-phosphate-acyltransferase (see Frentzen, 1998, Lipid, 100(4-5):161-166).

For publications on plant fatty acid biosynthesis, desaturation, lipid metabolism and membrane transport of lipoic compounds, beta-oxidation, fatty acid modification and cofactors, triacylglycerol storage and assembly including references therein see following articles: Kinney, 1997, Genetic Engineering, ed.: J K Setlow, 19:149-166; Ohlrogge and Browse, 1995, Plant Cell 7:957-970; Shanklin and Cahoon, 1998, Annu. Rev. Plant Physiol. Plant Mol. Biol., 49:611-641; Voelker, 1996, Genetic Engineering, ed.: J K Setlow, 18:111-13; Gerhardt, 1992, Prog. Lipid R. 31:397-417; Gühnemann-Schäfer & Kindl, 1995, Biochim. Biophys Acta 1256:181-186; Kunau et al., 1995, Prog. Lipid Res. 34:267-342; Stymne et al 1993, in: Biochemistry and Molecular Biology of Membrane and Storrage Lipids of Plants, Eds: Murata and Somerville, Rockville, American Society of Plant Physiologists, 150-158, Murphy & Ross 1998, Plant Journal. 13(1):1-16.

Vitamins, cofactors, and nutraceuticals such as PUFAs comprise a group of molecules which the higher animals have lost the ability to synthesize and so must ingest or which the higher animals cannot sufficiently produce on their own and so must ingest additionally, although they are readily synthesized by other organisms such as bacteria. The biosynthesis of these molecules in organisms capable of producing them, such as bacteria, has been largely characterized (Ullmann's Encyclopedia of Industrial Chemistry, Vitamins vol. A27, p. 443-613, VCH: Weinheim, 1996; Michal, G. (1999) Biochemical Pathways: An Atlas of Biochemistry and Molecular Biology, John Wiley & Sons; Ong, A. S., Niki, E. & Packer, L. (1995) Nutrition, Lipids, Health, and Disease Proceedings of the UNESCO/Confederation of Scientific and Technological Associations in Malaysia, and the Society for Free Radical Research Asia, held Sep. 1-3, 1994 at Penang, Malaysia, AOCS Press: Champaign, Ill. X, 374 S).

These said molecules are either bioactive substances themselves, or are precursors of biologically active substances which may serve as electron carriers or intermediates in a variety of metabolic pathways. Aside from their nutritive value, these compounds also have significant industrial value as coloring agents, antioxidants, and catalysts or other processing aids. (For an overview of the structure, activity, and industrial applications of these compounds, see, for example, Ullmann's Encyclopedia of Industrial Chemistry, Vitamins vol. A27, p. 443-613, VCH: Weinheim, 1996.). Polyunsaturated fatty acids have various functions and health benefit effects such as in coronary heart disease, inflammatory mechanisms, infant nutrition etc. For publications and references see including references cited therein: Simopoulos 1999, Am. J. Clin. Nutr., 70 (3 Suppl):560-569, Takahata et al., Biosc. Biotechnol. Biochem, 1998, 62 (11):2079-2085, Willich und Winther, 1995, Deutsche Medizinische Wochenschrift, 120 (7):229 ff.

II. Elements and Methods of the Invention

The present invention is based, at least in part, on the discovery of novel molecules, referred to herein as ASE nucleic acid and protein molecules, which have an effect on the production of cellular membranes in *Isochrysis galbana* and influence for example the movement of molecules across such membranes. In one embodiment, the ASE molecules participate in the metabolism of compounds necessary for the construction of cellular membranes in microorganisms and plants, or directly influence the transport of molecules across these membranes. In a preferred embodiment, the activity of the ASE molecules of the present invention to regulate membrane component production and membrane transport has an impact on the production of a desired fine chemical by this organism. In a particularly preferred embodiment, the ASE molecules of the invention are modulated in activity, such that the microorganisms' or plants' metabolic pathways which the ASEs of the invention regulate are modulated in yield, production, and/or efficiency of production and the transport of compounds through the membranes is altered in efficiency, which either directly or indirectly modulates the yield, production, and/or efficiency of production of a desired fine chemical by microorganisms and plants.

The language, ASE or ASE polypeptide, includes proteins which participate in the metabolism of compounds necessary for the construction of cellular membranes in microorganisms and plants, or in the transport of molecules across these membranes. Examples of ASEs are disclosed in SEQ ID NO: 1 or its derivatives. The terms ASE gene or ASE nucleic acid sequence include nucleic acid sequences encoding an ASE, which consist of a coding region and also corresponding untranslated 5' and 3' sequence regions.

Examples of ASE genes include those set forth in SEQ ID NO: 1 and their derivatives. The terms production or productivity are art-recognized and include the concentration of the fermentation product (for example, the desired fine chemical) formed within a given time and a given fermentation volume (e.g., kg product per hour per liter). The term efficiency of production includes the time required for a particular level of production to be achieved (for example, how long it takes for the cell to attain a particular throughput of a fine chemical). The term yield or product/carbon yield is art-recognized and includes the efficiency of the conversion of the carbon source into the product (i.e., fine chemical). This is generally written as, for example, kg product per kg carbon source. By increasing the yield or production of the compound, the quantity of recovered molecules, or of useful recovered molecules, of that compound in a given amount of culture over a given amount of time is increased. The terms biosynthesis or a biosynthetic pathway are art-recognized and include the synthesis of a compound, preferably an organic compound, by a cell from intermediate compounds in what may be a multistep and highly regulated process. The terms degradation or a degradation pathway are art-recognized and include the breakdown of a compound, preferably an organic compound, by a cell to degradation products (generally speaking, smaller or less complex molecules) in what may be a multistep and highly regulated process. The language metabolism is art-recognized and includes the totality of the biochemical reactions that take place in an organism. The metabolism of a particular compound, then, (e.g., the metabolism of a fatty acid) comprises the overall biosynthetic, modification, and degradation pathways in a cell related to this compound.

In another embodiment, the ASE molecules of the invention are capable of modulating the production of a desired molecule, such as a fine chemical, in microorganisms or plants. There are a number of mechanisms by which the alteration of an ASE of the invention may directly affect the yield, production, and/or efficiency of production of a fine chemical from a microorganism or plant strain incorporating such an altered protein. Those ASEs involved in the transport of fine chemical molecules within or from the cell may be increased in number or activity such that greater quantities of these compounds are transported across membranes, from which they are more readily recovered and interconverted. Further, fatty acids and lipids themselves are desirable fine chemicals; by optimizing the activity or increasing the number of one or more ASEs of the invention which participate in the biosynthesis of these compounds, or by impairing the activity of one or more ASEs which are involved in the degradation of these compounds, it may be possible to increase the yield, production, and/or efficiency of production of fatty acid and lipid molecules from microorganisms or plants.

The mutagenesis of the ASE gene of the invention may also result in ASEs having altered activities which indirectly impact on the production of one or more desired fine chemicals from microorganisms or plants. For example, ASEs of the invention involved in the export of waste products may be increased in number or activity such that the normal metabolic wastes of the cell (possibly increased in quantity due to the overproduction of the desired fine chemical) are efficiently exported before they are able to damage molecules within the cell (which would decrease the viability of the cell) or to interfere with fine chemical biosynthetic pathways (which would decrease the yield, production, or efficiency of production of the desired fine chemical). Further, the relatively large intracellular quantities of the desired fine chemical may in themselves be toxic to the cell, so by increasing the activity or number of transporters able to export this compound from the cell, one may increase the viability of the cell in culture, in turn leading to a greater number of cells in the culture producing the desired fine chemical. The ASEs of the invention may also be manipulated such that the relative amounts of different lipid and fatty acid molecules are produced. This may have a profound effect on the lipid composition of the membrane of the cell. Since each type of lipid has different physical properties, an alteration in the lipid composition of a membrane may significantly alter membrane fluidity. Changes in membrane fluidity can impact the transport of molecules across the membrane, as well as the integrity of the cell, both of which have a profound effect on the production of fine chemicals from microorganisms and plants in large-scale fermentative culture. Plant membranes confer specific characteristics such as tolerance towards heat, cold, salt, drought and tolerance towards pathogens like bacteria and fungi. Modulating membrane compounds therefore can have a profound effect on the plants' fitness to survive under aforementioned stress parameters. This can happen either via changes in signaling cascades or directly via the changed membrane composition (for example see: Chapman, 1998, Trends in Plant Science, 3 (11):419-426) and influence signaling cascades (see Wang 1999, Plant Physiology, 120:645-651) or on cold tolerance as disclosed in WO 95/18222.

The isolated nucleic acid sequence of the invention is contained within the genome of an *Isochrysis galbana* strain as described in the Examples. The nucleotide sequence of the isolated *Isochrysis galbana* ASE cDNA and the predicted amino acid sequences of the *Isochrysis galbana* ASEs are shown in SEQ ID NO: 1 and 2, respectively.

A fragment of nucleic acid molecule in SEQ ID NO: 1 was isolated by polymerase chain reaction with the aid of degenerated oligonucleotides derived from other known elongase genes and a vector primer. A partial fragment was amplified further and used for the isolation of a full length cDNA containing sufficient sequence information representing a functionally active ASE gene. One clone contained a complete ASE gene showing weak homology to known elongase genes. The expression of the open reading frame in yeast unforeseeingly revealed an ASE gene specific activity. The enzyme elongates Δ9-fatty acids as shown in the Examples.

The present invention also pertains to proteins which have an amino acid sequence which is substantially homologous to an amino acid sequence of SEQ ID NO: 2. As used herein, a protein which has an amino acid sequence which is substantially homologous to a selected amino acid sequence is at least about 50% homologous to the selected amino acid sequence, e.g., the entire selected amino acid sequence. A protein which has an amino acid sequence which is substantially homologous to a selected amino acid sequence can also be least about 50-60%, preferably at least about 60-70%, and more preferably at least about 70-80%, 80-90%, or 90-95%, and most preferably at least about 96%, 97%, 98%, 99% or more homologous to the selected amino acid sequence.

The ASE of the invention or a biologically active portion or fragment thereof can participate in the metabolism of compounds necessary for the construction of cellular membranes in microorganisms or plants, or in the transport of molecules across these membranes, or have one or more of the activities needed to elongate C18 PUFAs to yield in $C_{22}$ or $C_{24}$ PUFAs as well as related PUFAs.

Various aspects of the invention are described in further detail in the following subsections:

A. Isolated Nucleic Acid Molecules

One aspect of the invention pertains to isolated nucleic acid molecules that encode ASE polypeptides or biologically active portions thereof, as well as nucleic acid fragments sufficient for use as hybridization probes or primers for the identification or amplification of ASE-encoding nucleic acid (e.g., ASE DNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. This term also encompasses untranslated sequences located at both the 3' and 5' ends of the coding region of the gene: at least about 500, preferably at least about 400, more preferably at least about 350, 300, 250, 200, 150 and even more preferably at least about 100 nucleotides of sequence upstream from the 5' end of the coding region and at least about 1000, preferably at least about 500, more preferably at least about 400, 300, 250, 200, 150 and even more preferably 100, 80, 60, 40 or 20 nucleotides of sequence downstream from the 3' end of the coding region of the gene. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated ASE nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g, an *Isochrysis galbana* cell). Moreover, an "isolated" nucleic acid molecule, such as a cDNA molecule, can be substantially free of other cellular material, or-culture medium when produced by recombinant techniques, or chemical precursors or other chemicals when chemically synthesized; the language "substantially free of cellular material" includes preparations of nucleic acid molecules having less than about 30% (by dry weight) of other material such as proteins, polysaccharides etc. (also referred to herein as a "contaminating material"), more preferably less than about 20% of contaminating material, still more preferably less than about 10% of contaminating material, and most preferably less than about 5% of contaminating material.

One embodiment of the invention is an isolated nucleic acid derived from a plant encoding a polypeptide which elongates α-linolenic acid ($C_{18:3\ \Delta 9,\ 12,\ 15}$) by at least two carbon atoms whereas γ-linolenic acid ($C_{18:3\ \Delta 6,\ 9,\ 12}$) is not elongated.

A further embodiment of the invention is an isolated nucleic acid comprising a nucleotide sequence which encodes a polypeptide which elongates α-linolenic acid ($C_{18:3\ \Delta 9,\ 12,\ 15}$) by at least two carbon atoms whereas γ-linolenic acid ($C_{18:3\ \Delta 6,\ 9,\ 12}$) is not elongated, which nucleic acid is selected from the group consisting of a) a nucleic acid sequence depicted in SEQ ID NO: 1, b) a nucleic acid sequence which encodes a polypeptide depicted in SEQ ID NO: 2, c) derivatives of the sequence depicted in SEQ ID NO: 1, which encodes polypeptides having at least 50% homology to the sequence encoding amino acid sequences depicted in SEQ ID NO: 2 and which sequences function as an elongase.

The abovementioned isolated nucleic acid of the invention is derived from organisms such as ciliates, fungi, algae or dinoflagellates which are able to synthesize PUFAs, preferably from plants, particularly preferably from the genus *Isochrysis* and most particularly preferably from *Isochrysis galbana*.

One aspect of the invention pertains to isolated nucleic acid molecules that encode ASE polypeptides or biologically active portions thereof, as well as nucleic acid fragments sufficient for use as hybridization probes or primers for the identification or amplification of ASE-encoding nucleic acid (e.g., ASE DNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. This term also encompasses the untranslated sequence located at both the 3' and 5' ends of the coding region of the gene: at least about 100 nucleotides of sequence upstream from the 5' end of the coding region and at least about 20 nucleotides of sequence downstream from the 3' end of the coding region of the gene. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated ASE nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g, an *Isochrysis galbana* cell). Moreover, an "isolated" nucleic acid molecule, such as a cDNA molecule, can be substantially free of other cellular material, or culture medium when produced by recombinant techniques, or chemical precursors or other chemicals when chemically synthesized. Substantially free means that the [lacuna]

A nucleic acid molecule of the present invention, e.g., a nucleic acid molecule having a nucleotide sequence of SEQ ID NO: 1, or a portion thereof, can be isolated using standard molecular biology techniques and the sequence information provided herein. For example, an *Isochrysis galbana* ASE cDNA can be isolated from an *Isochrysis galbana* library using all or a portion of SEQ ID NO: 1 as a hybridization probe and standard hybridization techniques (e.g., as described in Sambrook et al., Molecular Cloning: A Laboratory Manual. 2nd, ed., Cold Spring Harbor Laboratory, Cold Spring Harbor Laboratory Press, Cold Spring Harbor, N.Y., 1989). Moreover, a nucleic acid molecule encompassing all or a portion of one of the sequences of SEQ ID NO: 1 can be isolated by the polymerase chain reaction using oligonucleotide primers designed on the basis of this sequence or parts thereof, especially regions around his-box motifs, see Shanklin et al. (1994) Biochemistry 33, 12787-12794 (e.g., a nucleic acid molecule encompassing all or a portion of one of the sequences of SEQ ID NO: 1 can be isolated by the polymerase chain reaction using oligonucleotide primers designed on the basis of this same sequence of SEQ ID NO: 1). For example, mRNA can be isolated from plant cells (e.g., by the guanidinium-thiocyanate extraction procedure of Chirgwin et al. (1979) Biochemistry 18: 5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed on the basis of one of the nucleotide sequence shown in SEQ ID NO: 1. A nucleic acid of the invention can be amplified using cDNA or, alternatively, genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to an ASE nucleotide sequence can be prepared by standard synthetic techniques, e.g., using an automated DNA synthesizer.

The cDNA shown in SEQUENCE ID NO: 1 comprises sequences encoding ASEs (i.e., the "coding region"), as well as 5' untranslated sequence and 3' untranslated sequence information. Alternatively, the nucleic acid molecule can comprise only the coding region of any of the sequences in SEQ ID NO: 1 or can contain whole genomic fragments isolated from genomic DNA.

The SEQUENCE ID NO: 2 is a translation of the coding region of the nucleotide sequence of nucleic acid molecule Ig_ASE1 shown in SEQ ID NO: 1.

In another preferred embodiment, an isolated nucleic acid molecule of the invention comprises a nucleic acid molecule which is a complement of one of the nucleotide sequences shown in SEQ ID NO: 1, or a portion thereof. A nucleic acid molecule which is complementary to one of the nucleotide sequences shown in SEQ ID NO: 1 is one which is sufficiently complementary to one of the nucleotide sequences shown in SEQ ID NO: 1 such that it can hybridize with one of the nucleotide sequences shown in SEQ ID NO: 1, thereby forming a stable duplex.

Homologs of the novel elongase nucleic acid sequence having the sequence SEQ ID NO: 1 mean, for example, allelic variants which have at least about 50-60%, preferably at least about 60-70%, more preferably at least about 70-80%, 80-90%, or 90-95%, and even more preferably at least about 95%, 96%, 97%, 98%, 99% or more homology to a nucleotide sequence shown in SEQ ID NO: 1 or its homologs, derivatives or analogs or portions thereof. In an additional preferred embodiment, an isolated nucleic acid molecule of the invention comprises a nucleotide sequence which hybridizes, e.g., hybridizes under stringent conditions, with one of the nucleotide sequences shown in SEQ ID NO: 1, or a portion thereof. Allelic variants comprise, in particular, functional variants which are obtainable by deletion, insertion or substitution of nucleotides from the sequence depicted in SEQ ID NO: 1, the intention being, however, that the enzymatic activity of the derived synthesized proteins advantageously be retained for the insertion of one or more genes. Proteins which have still the enzymatic activity of the elongase means proteins which have at least 10% of the original enzymatic activity, preferably 20%, particularly preferably 30%, most particularly preferably 40%, in comparison to the protein encoded by SEQ ID NO: 2.

Homologs of SEQ ID NO: 1 additionally mean, for example, bacterial, fungal or plant homologs, truncated sequences, single-stranded DNA or RNA of the coding and noncoding DNA sequence.

Homologs of SEQ ID NO: 1 also mean derivatives such as, for example, promoter variants. The promoters upstream of the indicated nucleotide sequences may be modified by one or more nucleotide exchanges, by insertion(s) and/or deletion(s) without, however, the functionality or activity of the promoters being impaired. It is additionally possible for the promoters to have their activity increased by modifying their sequence, or to be completely replaced by more active promoters even from heterologous organisms.

Moreover, the nucleic acid molecule of the invention can comprise only a portion of the coding region of one of the sequences in SEQ ID NO: 1, for example a fragment which can be used as a probe or primer or a fragment encoding a biologically active portion of an ASE. The nucleotide sequences determined from the cloning of the ASE gene from *Isochrysis galbana* allow for the generation of probes and primers designed for use in identifying and/or cloning ASE homologs in other cell types and organisms, as well as ASE homologs from *Isochrysis galbana* or related species. The probe/primer typically comprises substantially purified oligonucleotide. The oligonucleotide typically comprises a region of nucleotide sequence that hybridizes under stringent conditions with at least about 12, preferably about 16, more preferably about 25, 40, 50 or 75 consecutive nucleotides of a sense strand of one of the sequences set forth in SEQUENCE ID NO: 1, an antisense sequence of one of the sequences set forth in sequence ID NO: 1, or naturally occurring mutants thereof. Primers based on a nucleotide sequence of SEQUENCE ID NO: 1 can be used in PCR reactions to clone ASE homologs. Probes based on the ASE nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which misexpress an ASE, such as by measuring a level of an ASE-encoding nucleic acid in a sample of cells, e.g., detecting ASE mRNA levels or determining whether a genomic ASE gene has been mutated or deleted.

In one embodiment, the nucleic acid molecule of the invention encodes a protein or portion thereof which includes an amino acid sequence which is sufficiently homologous to an amino acid sequence of SEQ ID NO: 2 such that the protein or portion thereof maintains the ability to participate in the metabolism of compounds necessary for the construction of cellular membranes in microorganisms or plants, or in the transport of molecules across these membranes. As used herein, the term "sufficiently homologous" refers to proteins or portions thereof which have amino acid sequences which include a minimum number of identical or equivalent (e.g., an amino acid residue which has a similar side chain as an amino acid residue in one of the sequences of SEQ ID NO: 2) amino acid residues to an amino acid sequence of SEQ ID NO: 2 such that the protein or portion thereof is able to participate in the metabolism of compounds necessary for the construction of cellular membranes in microorganisms or plants, or in the transport of molecules across these membranes. Protein members of such membrane component metabolic pathways or membrane transport systems, as described herein, may play a role in the production and secretion of one or more fine chemicals. Examples of such activities are also described herein. Thus, the function of an ASE contributes either directly or indirectly to the yield, production, and/or efficiency of production of one or more fine chemicals. Examples of ASE substrate specificities of the catalytic activity are set forth in Tab. 2.

In another embodiment, derivatives of the nucleic acid molecule of the invention encode proteins which are at least about 50-60%, preferably at least about 60-70%, and more preferably at least about 70-80%, 80-90%, 90-95%, and most preferably at least about 96%, 97%, 98%, 99% or more homologous to an entire amino acid sequence of SEQ ID NO: 2.

Portions of proteins encoded by the ASE nucleic acid molecules of the invention are preferably biologically active portions of one of the ASEs. As used herein, the term "biologically active portion of an ASE" is intended to include a portion, e.g., a domain/motif, of an ASE that participates in the metabolism of compounds necessary for the construction of cellular membranes in microorganisms or plants, or in the transport of molecules across these membranes, or has an activity as set forth in Tab. 2. To determine whether an ASE or a biologically active portion thereof can participate in the metabolism of compounds necessary for the construction of cellular membranes in microorganisms or plants, or in the transport of molecules across these membranes, an assay of enzymatic activity may be performed. Such assay methods are well known to those skilled in the art, as detailed in Example 8 of the Examples.

Additional nucleic acid fragments encoding biologically active portions of an ASE can be prepared by isolating a portion of one of the sequences in SEQ ID NO: 2, expressing the encoded portion of the ASE or peptide (e.g., by recombinant expression in vitro) and assessing the activity of the encoded portion of the ASE or peptide.

The invention further encompasses nucleic acid molecules that differ from one of the nucleotide sequences shown in SEQ ID NO: 1 (and portions thereof) due to degeneracy of the genetic code and thus encode the same ASE as that encoded by the nucleotide sequences shown in SEQ ID NO: 1. In another embodiment, an isolated nucleic acid molecule of the invention has a nucleotide sequence encoding a protein having an amino acid sequence shown in SEQ ID NO: 2. In a further embodiment, the nucleic acid molecule of the invention encodes a full length *Isochrysis galbana* protein which is substantially homologous to an amino acid sequence of SEQ ID NO: 2 (encoded by an open reading frame shown in SEQ ID NO: 1).

In addition to the *Isochrysis galbana* ASE nucleotide sequences shown in SEQ ID NO: 1, it will be appreciated by those skilled in the art that DNA sequence polymorphisms that lead to changes in the amino acid sequences of ASEs may exist within a population (e.g., the *Isochrysis galbana* population). Such genetic polymorphisms in the ASE gene may exist among individuals within a population due to natural variation. As used herein, the terms "gene" and "recombinant gene" refer to nucleic acid molecules comprising an open reading frame encoding an ASE, preferably an *Isochrysis galbana* ASE. Such natural variations can typically result in 1-5% variance in the nucleotide sequence of the ASE gene. Any and all such nucleotide variations and resulting amino acid polymorphisms in ASE that are the result of natural variation and that do not alter the functional activity of ASEs are intended to be within the scope of the invention.

Nucleic acid molecules corresponding to natural variants and non-*Isochrysis galbana* homologs of the *Isochrysis galbana* ASE cDNA of the invention can be isolated based on their homology to *Isochrysis galbana* ASE nucleic acid disclosed herein using the *Isochrysis galbana* cDNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising a nucleotide sequence of SEQ ID NO: 1. In other embodiments, the nucleic acid is at least 25, 50, 100, 250 or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in Current Protocols in Molecular Biology, John Wiley & Sons, New York (1989), 6.3.1-6.3.6. A preferred, nonlimiting example of stringent hybridization conditions is hybridization in 6× sodium chloride/sodium citrate (SSC) at about 45 degree C., followed by one or more washes in 0.2×SSC, 0.1% SDS at 50-65 degree C. Preferably, an isolated nucleic acid molecule of the invention that hybridizes under stringent conditions to a sequence of SEQ ID NO: 1 corresponds to a naturally-occurring nucleic acid molecule. As used herein, a "naturally-occurring" nucleic acid molecule refers to an RNA or DNA molecule having a nucleotide sequence that occurs in nature, (e.g., encodes a natural protein). In one embodiment, the nucleic acid encodes a natural *Isochrysis galbana* ASE.

In addition to naturally-occurring variants of the ASE sequence that may exist in the population, the skilled artisan will further appreciate that changes can be introduced by mutation into a nucleotide sequence of SEQ ID NO: 1, thereby leading to changes in the amino acid sequence of the encoded ASE, without altering the functional ability of the ASE. For example, nucleotide substitutions leading to amino acid substitutions at "nonessential" amino acid residues can be made in a sequence of SEQ ID NO: 1. A "nonessential" amino acid residue is a residue that can be altered from a wild-type sequence of one of the ASEs (SEQ ID NO: 2) without altering the activity of said ASE, whereas an "essential" amino acid residue is required for ASE activity. Other amino acid residues, however, (e.g., those that are not conserved or only semiconserved in the domain having ASE activity) may not be essential for activity and thus are likely to be amenable to alteration without altering ASE activity.

Accordingly, another aspect of the invention pertains to nucleic acid molecules encoding ASEs that contain modified amino acid residues that are not essential for ASE activity. Such ASEs differ in amino acid sequence from a sequence contained in SEQ ID NO: 2 yet retain at least one of the ASE activities described herein. In one embodiment, the isolated nucleic acid molecule comprises a nucleotide sequence encoding a protein, wherein the protein comprises an amino acid sequence at least about 50% homologous to an amino acid sequence of SEQ ID NO: 2 and is capable of participation in the metabolism of compounds necessary for the construction of cellular membranes in *Isochrysis galbana*, or in the transport of molecules across these membranes, or has one or more activities set forth in Tab. 2. Preferably, the protein encoded by the nucleic acid molecule is at least about 50-60% homologous to one of the sequences in SEQUENCE ID NO: 2, more preferably at least about 60-70% homologous to one of the sequences in SEQ ID NO: 2, even more preferably at least about 70-80%, 80-90%, 90-95% homologous to one of the sequences in SEQUENCE ID NO: 2, and most preferably at least about 96%, 97%, 98%, or 99% homologous to one of the sequences in SEQ ID NO: 2.

To determine the percent homology of two amino acid sequences (e.g., one of the sequences of SEQ ID NO: 2 and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the sequences of SEQ ID NO: 2) is occupied by the same amino acid residue or nucleotide as the corresponding position in the other sequence (e.g., a mutant form of the form selected from SEQ ID NO: 2), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=numbers of identical positions/total numbers of positions×100).

An isolated nucleic acid molecule encoding an ASE homologous to a protein sequence of SEQ ID NO: 2 can be created by introducing one or more nucleotide substitutions, additions or deletions into a nucleotide sequence of SEQ ID NO: 1 such that one or more amino acid substitutions, additions or deletions are introduced into the encoded protein. Mutations can be introduced into one of the sequences of SEQ ID NO: 1 or its derivatives by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an ASE is preferably replaced with another amino acid residue from the same side chain family. Alternatively, in another embodiment, mutations can be introduced randomly along all or part of the ASE coding sequence, such as by saturation mutagenesis, and the resultant mutants can be screened for an ASE activity described herein to identify mutants that retain ASE activity. Following mutagenesis of one of the sequences of SEQ ID NO: 1, the encoded protein can be expressed recombinantly and the activity of the protein can be determined using, for example, assays described herein (see Examples).

A further known technique for directed evolution and mutagenesis of gene sequences encoding enzymes is gene shuffling (Stemmer, PNAS 1994, 91: 10747-10751, WO 97/20078 and WO 98/13487). Gene shuffling is a method for the combination of gene fragments and can be combined with error prone PCR in order to further enhance the genetic variability of resulting sequences and encoded enzymatic activities. A premise for such an approach is a suitable screening system. In the case of elongases high throughput metabolite measurements facilitated by MALDI-TOF, gas chromatography-mass spectroscopy, thin layer chromatography or liquid chromatography-mass spectroscopy or other suitable combinations or methods can be used to monitor the appearance of new compounds or products in the hydrophobic fraction.

In addition to the nucleic acid molecules encoding ASEs described above, another aspect of the invention pertains to isolated nucleic acid molecules which are antisense to an isolated nucleic acid comprising a nucleotide sequence which encodes a polypeptide which elongates α-linolenic acid ($C_{18:3\ \Delta 9, 12, 15}$) by at least two carbon atoms whereas γ-linolenic acid ($C_{18:3\ \Delta 6, 9, 12}$) is not elongated, selected from the group consisting of
a) a nucleic acid sequence depicted in SEQ ID NO: 1,
b) a nucleic acid sequence which encodes a polypeptide depicted in SEQ ID NO: 2,
c) derivatives of the sequence depicted in SEQ ID NO: 1, which encodes polypeptides having at least 50% homology to the sequence encoding amino acid sequences depicted in SEQ ID NO: 2 and which sequences function as an elongase.

An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can form hydrogen bonds with a sense nucleic acid. The antisense nucleic acid can be complementary to an entire ASE coding strand, or to only a portion thereof. In one embodiment, an antisense nucleic acid molecule is antisense to a "coding region" of the coding strand of a nucleotide sequence encoding an ASE. The term "coding region" refers to the region of the nucleotide sequence comprising codons which are translated into amino acid residues (e.g., the entire coding region starting with and ending with the stop codon, i.e. the last codon before the stop codon). In another embodiment, the antisense nucleic acid molecule is antisense to a "noncoding region" of the coding strand of a nucleotide sequence encoding ASE. The term "noncoding region" refers to 5' and 3' sequences which flank the coding region that are not translated into amino acids (i.e., also referred to as 5' and 3' untranslated regions). It is also possible to use the inverted repeat technology combining an antisense fragment with a portion of the antisense fragment in sense orientation linked by either an adapter sequence or an excisable intron (Abstract Book of the 6$^{th}$ Intern. Congr. Of Plant Mol Biol. ISPMB, Quebec Jun. 18-24, 2000, Abstract No. S20-9 by Green et al.).

Given the coding strand sequences encoding the ASE disclosed herein (e.g., the sequences set forth in SEQ ID NO: 1), antisense nucleic acids of the invention can be designed according to the rules of Watson and Crick base pairing. The antisense nucleic acid molecule can be complementary to the entire coding region of ASE mRNA, but more preferably is an oligonucleotide which is antisense to only a portion of the coding or noncoding region of ASE mRNA. For example, the antisense oligonucleotide can be complementary to the region surrounding the translation start site of ASE mRNA. An antisense oligonucleotide can be, for example, about 5, 10, 15, 20, 25, 30, 35, 40, 45 or 50 and more nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding an ASE to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on the selected cell surface, e.g., by linking the antisense nucleic acid molecule to a peptide or an antibody which binds to a cell surface receptor or antigen. The antisense nucleic acid molecule can also be delivered to cells using the vectors described below. To achieve sufficient intracellular concentrations of the antisense molecules, vector constructs in which the antisense nucleic acid molecule is placed under the control of a strong prokaryotic, viral, or eukaryotic promoter, including plant promoters, are preferred.

In another embodiment, the antisense nucleic acid molecule of the invention is an anomeric nucleic acid molecule. An anomeric nucleic acid molecule forms specific double-stranded hybrids with complementary RNA in which, contrary to the usual units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analog (Inoue et al. (1987) FEBS Lett. 215:327-330).

In another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585-591)) can be used to catalytically cleave ASE mRNA transcripts to thereby inhibit translation of ASE mRNA. A ribozyme having specificity for an ASE-encoding nucleic acid can be designed on the basis of the nucleotide sequence of an ASE cDNA disclosed herein in SEQ ID NO: 1 or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in an ASE-encoding mRNA. See, e.g., Cech et al. U.S. Pat. No. 4,987,071 and Cech et al. U.S. Pat. No. 5,116, 742. Alternatively, ASE mRNA can be used to select a catalytic RNA having a specific ribonuclease activity from a pool of RNA molecules. See, e.g., Bartel, D. and Szostak, J. W. (1993) Science 261:1411-1418.

Alternatively, ASE gene expression can be inhibited by targeting nucleotide sequences complementary to the regulatory region of an ASE nucleotide sequence (e.g., an ASE promoter and/or enhancers) to form triple helical structures that prevent transcription of an ASE gene in target cells. See generally Helene, C. (1991) Anticancer Drug Res. 6(6):569-84; Helene, C. et al. (1992) Ann. N.Y. Acad. Sci. 660:27-36; and Maher, L. J. (1992) Bioassays 14(12):807-15.

B. Gene Construct

Another embodiment of the invention is a novel gene construct comprising an isolated nucleic acid derived from a plant which encodes a polypeptide which elongates α-linolenic acid ($C_{18:3\ \Delta 9,\ 12,\ 15}$) by at least two carbon atoms but not γ-linolenic acid ($C_{18:3\ \Delta 6,\ 9,\ 12}$), or the gene sequence of SEQ ID NO: 1, its homologs, derivatives or analogs as defined above which have been functionally linked to one or more regulatory signals, advantageously to increase gene expression. Examples of these regulatory sequences are sequences to which inducers or repressors bind and thus regulate the expression of the nucleic acid. In addition to these novel regulatory sequences, the natural regulation of these sequences in front of the actual structural genes can still be present and, where appropriate, have been genetically modified so that the natural regulation has been switched off and the expression of the genes has been increased. The gene construct can, however, also have a simpler structure, that is to say no additional regulatory signals have been inserted in front of the sequence SEQ ID NO: 1 or its homologs, and the natural promoter with its regulation has not been deleted. Instead, the natural regulatory sequence has been mutated so that regulation no longer takes place, and gene expression is enhanced. The gene construct may additionally advantageously comprise one or more so-called enhancer sequences functionally linked to the promoter and making increased expression of the nucleic acid sequence possible. It is also possible to insert at the 3' end of the DNA sequences additional advantageous sequences, such as further regulatory elements or terminators. The elongase genes may be present in one or more copies in the gene construct. It is advantageous for further genes to be present in the gene construct for insertion of further genes into organisms.

Advantageous regulatory sequences for the novel process are present, for example, in promoters such as cos-, tac-, trp-, tet-, trp-tet-, lpp-, lac-, lpp-lac-, lacI$^q$-, T7-, T5-, T3-, gal-, trc-, ara-, SP6-, λ-$P_R$- or λ-$P_L$-promoter and are advantageously used in Gram-negative bacteria. Further advantageous regulatory sequences are present, for example, in the Gram-positive promoters amy and SP02, in the yeast or fungal promoters ADC1, MFα, AC, P-60, CYC1, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Also advantageous in this connection are inducible promoters such as the promoters described in EP-A-0 388 186 (benzenesulfonamide-inducible), Plant J. 2, 1992: 397-404 (Gatz et al., tetracyclin-inducible), EP-A-0 335 528 (abscisic acid-inducible) or WO 93/21334 (ethanol or cyclohexenol inducible). Additional useful plant promoters are the cytosolic FBPase promoter or ST-LSI promoter of the potato (Stockhaus et al., EMBO J. 8, 1989, 2445), the phosphoribosylpyrophoshate amidotransferase promoter of Glycine max (gene bank accession No. U87999) or the node-specific promoter described in EP-A-0 249 676. Particularly advantageous promoters are promoters which allow the expression in tissues which are involved in the fatty acid biosynthesis. Most particularly advantageous are seed specific promoters such as usp-, LEB4-, phaseolin or napin promoter. Additional particularly advantageous promoters are seed-specific promoters which can be used for monocots or dicots and which are described in U.S. Pat. No. 5,608,152 (napin promoter from rapeseed), WO 98/45461 (phaseolin promoter from *Arabidopsis*), U.S. Pat. No. 5,504, 200 (phaseolin promoter from *Phaseolus vulgaris*), WO 91/13980 (Bce4 promoter from *Brassica*), Baeumlein et al., Plant J., 2, 2, 1992: 233-239 (LEB4 promoter from legumes); said promoters are useful in dicots. The following promoters are useful for example in monocotyledons: lpt-2- or lpt-1-promoter from barley (WO 95/15389 and WO 95/23230), hordein promoter from barley and other useful promoters described in WO 99/16890.

It is possible in principle to use all natural promoters with their regulatory sequences like those mentioned above for the novel process. It is also possible and advantageous in addition to use synthetic promoters.

The gene construct may, as described above, also comprise further genes which are to be inserted into the organisms. It is possible and advantageous to insert and express in host organisms regulatory genes such as genes for inducers, repressors or enzymes which intervene by their enzymatic activity in the regulation, or one or more or all genes of a biosynthetic pathway. These genes can be heterologous or homologous in origin. The inserted genes may have their own promoter or else be under the control of the promoter of the sequence SEQ ID NO: 1 or its homologs.

The gene construct advantageously comprises, for expression of the other genes present, additional 3' and/or 5' terminal regulatory sequences to enhance expression, which are selected for optimal expression depending on the selected host organism and gene or genes.

These regulatory sequences are intended to make specific expression of the genes and protein expression possible as mentioned above. This may mean, depending on the host organism, for example that the gene is expressed or overexpressed only after induction, or that it is immediately expressed and/or overexpressed.

The regulatory sequences or factors may moreover preferably have a beneficial effect on expression of the introduced genes, and thus increase it. It is possible in this way for the regulatory elements to be enhanced advantageously at the transcription level by using strong transcription signals such as promoters and/or enhancers. However, in addition, it is also possible to enhance translation by, for example, improving the stability of the mRNA.

In addition the inventive gene construct preferably comprises additional genes of different biochemical pathways, for example genes for the synthesis of vitamins, carotinoids, sugars such as monosaccharides, oligosaccharides or polysaccharides, or fatty acid biosynthesis genes, more preferably the gene construct comprises fatty acid biosynthesis genes such as desaturases, hydroxylases, Acyl-ACP-thioesterases, elongases, acetylenases, synthesases or reductases such as Δ19-, Δ17-, Δ15-, Δ12-, Δ9-, Δ8-, Δ6-, Δ5-, Δ4-desaturases, hydroxylases, elongases, Δ12-acetylenase, Acyl-ACP-thioesterasen, β-ketoacyl-ACP-synthases or β-ketoacyl-ACP-reductases. Preferably the gene construct comprises fatty acid biosynthesis genes selected from the group consisting of Δ19-, Δ17-, Δ15-, Δ12-, Δ9-, Δ8-, Δ6-, Δ5-, Δ4-desaturases, hydroxylases, elongases, Δ12-acetylenase, acyl-ACP-thioesterases, β-ketoacyl-ACP-synthases or β-ketoacyl-ACP-reductases.

C. Recombinant Expression Vectors and Host Cells

Another aspect of the invention pertains to vectors, preferably expression vectors, containing a nucleic acid encoding an ASE (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they have been introduced (e.g., bacterial vectors having a bacterial origin of replication and episomal mammalian vectors). Other vectors (e.g., nonepisomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise at least one inventive nucleic acid or at least one inventive gene construct of the invention in a form suitable for expression of the nucleic acid in a host cell, which means that the recombinant expression vectors include one or more regulatory sequences, selected on the basis of the host cells used for expression, which is or are linked operably to the nucleic acid sequence to be expressed. Within a recombinant expression vector, "linked operably" is intended to mean that the nucleotide sequence of interest is linked to the regulatory sequence(s) in a manner which allows for expression of the nucleotide sequence and these sequences are fused to each other so that both sequences fulfill the proposed function ascribed to the sequence used (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990) or see: Gruber and Crosby, in: Methods in Plant Molecular Biology and Biotechnolgy, CRC Press, Boca Raton, Fla., eds.: Glick and Thompson, Chapter 7, 89-108 including the references therein. Regulatory sequences include those which govern constitutive expression of a nucleotide sequence in many types of host cell and those which govern direct expression of the nucleotide sequence only in certain host cells under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., ASEs, mutant forms of ASEs, fusion proteins, etc.).

The recombinant expression vectors of the invention can be designed for expression of ASEs in prokaryotic or eukaryotic cells. For example, ASE genes can be expressed in bacterial cells such as *C. glutamicum*, insect cells (using baculovirus expression vectors), yeast and other fungal cells (see Romanos, M. A. et al. (1992) Foreign gene expression in yeast: a review, Yeast 8: 423-488; van den Hondel, C. A. M. J. J. et al. (1991) Heterologous gene expression in filamentous fungi, in: More Gene Manipulations in Fungi, J. W. Bennet & L. L. Lasure, eds., p. 396-428: Academic Press: San Diego; and van den Hondel, C. A. M. J. J. & Punt, P. J. (1991) Gene transfer systems and vector development for filamentous fungi, in: Applied Molecular Genetics of Fungi, Peberdy, J. F. et al., eds., p. 1-28, Cambridge University Press: Cambridge), algae (Falciatore et al., 1999, Marine Biotechnology. 1, 3:239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella,* and *Stylonychia*, especially of the genus *Stylonychia lemnae*, with vectors following a transformation method as described in WO9801572, and multicellular plant cells (see Schmidt, R. and Willmitzer, L. (1988), High efficiency *Agrobacterium tumefaciens*-mediated transformation of *Arabidopsis thaliana* leaf and cotyledon explants, Plant Cell Rep.: 583-586); Plant Molecular Biology and Biotechnology, C Press, Boca Raton, Fla., chapter 6/7, p. 71-119 (1993); F. F. White, B. Jenes et al., Techniques for Gene Transfer, in: Transgenic Plants, Vol. 1, Engineering and Utilization, eds.: Kung und R. Wu, Academic Press (1993), 128-43; Potrykus, Annu. Rev. Plant Physiol. Plant Molec. Biol. 42 (1991), 205-225 (and references cited therein) or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or nonfusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the elongase ASE is cloned into a pGEX expression vector to create a vector encoding a fusion protein comprising, from the N-terminus to the C-terminus, GST thrombin cleavage site X protein. The fusion protein can be purified by affinity chromatography using glutathione-agarose resin. Recombinant ASE unfused to GST can be recovered by cleavage of the fusion protein with thrombin.

Examples of suitable inducible nonfusion E. coli expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

Other vectors which are useful in prokaryotic organisms are known to a person skilled in the art; such vectors are for example in E. coli pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III$^{113}$-B1, λgt11 or pBdCI, in Streptomyces pIJ101, pIJ364, pIJ702 or pIJ361, in Bacillus pUB110, pC194 or pBD214, in Corynebacterium pSA77 or pAJ667.

One strategy to maximize recombinant protein expression is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in the bacterium chosen for expression, such as C. glutamicum (Wada et al. (1992) Nucleic Acids Res. 20:2111-2118). Such alteration of nucleic acid sequences of the invention can be carried out by standard DNA synthesis techniques.

In another embodiment, the ASE expression vector is a yeast expression vector. Examples of vectors for expression in yeast S. cerevisiae include pYepSec1 (Baldari, et al., (1987) Embo J. 6:229-234), pMFa (Kurjan and Herskowitz, (1982) Cell 30:933-943), pJRY88 (Schultz et al., (1987) Gene 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1-28, Cambridge University Press: Cambridge or in: More Gene Manipulations in Fungi [J. W. Bennet & L. L. Lasure, eds., p. 396-428: Academic Press: San Diego]. Additional useful yeast vectors are for example 2 µM, pAG-1, YEp6, YEp13 or pEMBLYe23.

Alternatively, the ASEs of the invention can be expressed in insect cells using baculovirus expression vectors. Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39).

The abovementioned vectors are only a small overview of possible useful vectors. Additional plasmids are well known by the skilled artisan and are described for example in: Cloning Vectors (Eds. Pouwels P. H. et al. Elsevier, Amsterdam-New York-Oxford, 1985, ISBN 0 444 904018).

In another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyomavirus, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Nonlimiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) PNAS 86:5473-5477), pancreas-specific promoters (Edlund et al. (1985) Science 230:912-916), and mammary gland-specific promoters (e.g., milk whey promoter; U.S. Pat. No. 4,873,316 and European Patent Application Publication No. 264,166). Developmentally-regulated promoters are also encompassed, for example the murine hox promoters (Kessel and Gruss (1990) Science 249:374-379) and the fetoprotein promoter (Campes and Tilghman (1989) Genes Dev. 3:537-546).

In another embodiment, the ASEs of the invention may be expressed in unicellular plant cells (such as algae), see Falciatore et al., 1999, Marine Biotechnology. 1 (3):239-251 and references therein, and plant cells from higher plants (e.g., the spermatophytes, such as crop plants). Examples of plant expression vectors include those detailed in: Becker, D., Kemper, E., Schell, J. and Masterson, R. (1992) "New plant binary vectors with selectable markers located proximal to the left border", Plant Mol. Biol. 20: 1195-1197; and Bevan, M. W. (1984) "Binary Agrobacterium vectors for plant transformation, Nucl. Acid. Res. 12: 8711-8721; Vectors for Gene Transfer in Higher Plants; in: Transgenic Plants, Vol. 1, Engineering and Utilization, eds.: Kung und R. Wu, Academic Press, 1993, p. 15-38.

A plant expression cassette preferably contains regulatory sequences capable of driving gene expression in plants cells and which are linked operably so that each sequence can fulfill its function such as termination of transcription, such as polyadenylation signals. Preferred polyadenylation signals are those originating from Agrobacterium tumefaciens T-DNA such as the gene 3 known as octopine synthase of the Ti-plasmid pTiACH5 (Gielen et al., EMBO J. 3 (1984), 835 ff) or functional equivalents thereof but also all other terminators functionally active in plants are suitable.

As plant gene expression is very often not limited on transcriptional levels a plant expression cassette preferably contains other operably linked sequences like translational enhancers such as the overdrive sequence containing the 5'-untranslated leader sequence from tobacco mosaic virus enhancing the protein per RNA ratio (Gallie et al 1987, Nucl. Acids Research 15:8693-8711).

Plant gene expression has to be linked operably to an appropriate promoter conferring gene expression in a time, cell or tissue specific manner. Preferred are promoters driving constitutive expression (Benfey et al., EMBO J. 8 (1989) 2195-2202) like those derived from plant viruses like the 35S CaMV (Franck et al., Cell 21 1980) 285-294), the 19S CaMV (see also U.S. Pat. No. 5,352,605 and WO 84/02913) or plant promoters like those from Rubisco small subunit described in U.S. Pat. No. 4,962,028. Additionally vATPase-gene promoters such as a 1153 basepair fragment from Beta vulgaris (Plant Mol Biol, 1999, 39:463-475) can be used to drive ASE gene expression alone or in combination with other PUFA biosynthesis genes.

Other preferred sequences for use in operable linkage in plant gene expression cassettes are targeting sequences necessary to direct the gene product in its appropriate cell compartment (for review see Kermode, Crit. Rev. Plant Sci. 15, 4 (1996), 285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells.

Plant gene expression can also be facilitated via a chemically inducible promoter (for review see Gatz 1997, Annu. Rev. Plant Physiol. Plant Mol. Biol., 48:89-108). Chemically inducible promoters are especially suitable if gene expression is wanted to occur in a time specific manner. Examples of such promoters are a salicylic acid inducible promoter (WO 95/19443), a tetracycline inducible promoter (Gatz et al., (1992) Plant J. 2, 397-404) and an ethanol inducible promoter (WO 93/21334).

Also promoters responding to biotic or abiotic stress conditions are suitable promoters such as the pathogen inducible PRP1 gene promoter (Ward et al., Plant. Mol. Biol. 22 (1993), 361-366), the heat inducible hsp80 promoter from tomato (U.S. Pat. No. 5,187,267), cold inducible alpha-amylase promoter from potato (WO 96/12814) or the wound-inducible pinII promoter (EP-A-0 375 091).

Especially those promoters are preferred which confer gene expression in tissues and organs where lipid and oil biosynthesis occurs, in seed cells such as cells of the endosperm and the developing embryo. Suitable promoters are the napin-gene promoter from rapeseed (U.S. Pat. No. 5,608,152), the USP-promoter from *Vicia faba* (Baeumlein et al., Mol Gen Genet, 1991, 225 (3):459-67), the oleosin-promoter from *Arabidopsis* (WO 98/45461), the phaseolin-promoter from *Phaseolus vulgaris* (U.S. Pat. No. 5,504,200), the Bce4-promoter from *Brassica* (WO 91/13980) or the legumin B4 promoter (LeB4; Baeumlein et al., 1992, Plant Journal, 2 (2):233-9) as well as promoters conferring seed specific expression in monocot plants like maize, barley, wheat, rye, rice etc. Suitable promoters to note are the lpt2 or lpt1-gene promoter from barley (WO 95/15389 and WO 95/23230) or those described in WO 99/16890 (promoters from the barley hordein-gene, the rice glutelin gene, the rice oryzin gene, the rice prolamin gene, the wheat gliadin gene, wheat glutelin gene, the maize zein gene, the oat glutelin gene, the *Sorghum kasirin*-gene, the rye secalin gene).

Also especially suited are promoters that confer plastid-specific gene expression as plastids are the compartment where precursors and some end products of lipid biosynthesis are synthesized. Suitable promoters such as the viral RNA-polymerase promoter are described in WO 95/16783 and WO 97/06250 and the clpP-promoter from *Arabidopsis* described in WO 99/46394.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PSE mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews*—Trends in Genetics, Vol. 1(1) 1986 and Mol et al., 1990, FEBS Letters 268:427-430.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an ASE can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

Vector DNA can be introduced into prokaryotic or eukaryotic cells via conventional transformation or transfection techniques. As used herein, the terms "transformation" and "transfection", conjugation and transduction are intended to refer to a variety of art-recognized techniques for introducing foreign nucleic acid (e.g., DNA) into a host cell, including calcium phosphate or calcium chloride coprecipitation, DEAE-dextran-mediated transfection, lipofection, natural competence, chemical-mediated transfer, or electroporation. Suitable methods for transforming or transfecting host cells including plant cells can be found in Sambrook, et al. (Molecular Cloning: A Laboratory Manual. 2nd ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as hygromycin and methotrexate or, in plants, those which confer resistance towards a herbicide such as imidazolinones, sulfonylurea, glyphosate or glufosinate. Nucleic acid encoding a selectable marker can be introduced into a host cell on the same vector as that encoding an ASE or can be introduced on a separate vector. Cells stably transfected with the introduced nucleic acid can be identified by, for example, drug selection (e.g., cells that have incorporated the selectable marker gene will survive, while the other cells die).

To create a homologously-recombinant microorganism, a vector is prepared which contains at least a portion of an ASE gene into which a deletion, addition or substitution has been introduced to thereby alter, e.g., functionally disrupt, the ASE gene. Preferably, this ASE gene is an *Isochrysis galbana* ASE gene, but it can be a homolog from a related plant or even from an alga, mammalian, yeast, or insect source. In a preferred embodiment, the vector is designed such that, upon homologous recombination, the endogenous ASE gene is functionally disrupted (i.e., no longer encodes a functional protein; also referred to as a knock-out vector). Alternatively, the vector can be designed such that, upon homologous recombination, the endogenous ASE gene is mutated or otherwise altered but still encodes a functional protein (e.g., the upstream regulatory region can be altered to thereby alter the expression of the endogenous ASE). To create a point mutation via homologous recombination also DNA-RNA hybrids can be used known as chimeraplasty known from Cole-Strauss et al. 1999, Nucleic Acids Research 27(5):1323-1330 and Kmiec, Gene therapy. 1999, American Scientist. 87(3): 240-247.

In the homologously-recombinant vector, the altered portion of the ASE gene is flanked at its 5' and 3' ends by additional nucleic acid of the ASE gene to allow for homologous recombination to occur between the exogenous ASE gene carried by a vector and an endogenous ASE gene in a microorganism or plant. The additional flanking ASE nucleic acid is of sufficient length for successful homologous recombination with the endogenous gene. Typically, several hundreds of basepairs up to kilobases of flanking DNA (both at the 5' and 3' ends) are included in the vector (see e.g., Thomas, K. R., and Capecchi, M. R. (1987) Cell 51: 503 for a description of homologous recombination vectors or Strepp et al., 1998, PNAS, 95 (8):4368-4373 for cDNA based recombination in *Isochrysis galbana*). The vector is introduced into a microorganism or plant cell (e.g., via *Agrobacterium* mediated gene transfer, biolistic transformation, polyethylene glycol or other applicable methods) and cells in which the introduced ASE gene has homologously recombined with the endogenous ASE gene are selected, using art-known techniques. In the case of plant cells the AHAS gene described in Ott et al., J. Mol. Biol. 1996, 263:359-360 is especially suitable for marker gene expression and resistance towards imidazolinone or sulfonylurea type herbicides.

In another embodiment, recombinant organisms such as microorganisms can be produced which contain selected systems which allow for regulated expression of the introduced gene. For example, inclusion of an ASE gene in a vector placing it under control of the Lac operon permits expression of the ASE gene only in the presence of IPTG. Such regulatory systems are well known in the art. Recombinant organisms means an organism which comprises an inventive nucleic acid sequence, a gene construct or a vector in the cell or inside the genome at a place which is not the "natural" place or at the "natural" place but modified in a manner which is not the natural manner; that means the coding sequence is modified and/or the regulatory sequence is modified. Modified means single nucleotides or one or more codons are changed in comparison to the natural sequence, preferably one ore more codons, more preferably one to six codons.

A host cell of the invention, such as a prokaryotic or eukaryotic host cell in culture, can be used to produce (i.e., express) an ASE. An alternate method can be applied in addition in plants by the direct transfer of DNA into developing flowers via electroporation or *Agrobacterium*-mediated gene transfer. Accordingly, the invention further provides methods for producing ASEs using the host cells of the invention. In one embodiment, the method comprises culturing the host cell of the invention (into which a recombinant expression vector encoding an ASE has been introduced, or into whose genome has been introduced a gene encoding a wild-type or altered ASE) in a suitable medium until ASE is produced. In another embodiment, the method further comprises isolating ASEs from the medium or the host cell.

Host cells suitable in principle to take up the nucleic acid of the invention, the novel gene construct or the inventive vector are all prokaryotic or eukaryotic organisms. The host organisms advantageously used are organisms such as bacteria, fungi, yeasts, animal or plant cells. Additional advantageous organisms are animals or preferably plants or parts thereof. Fungi, yeasts or plants are preferably used, particularly preferably fungi or plants, very particularly preferably plants such as oilseed plants containing high amounts of lipid compounds such as rapeseed, evening primrose, canola, peanut, linseed, soybean, safflower, sunflower, borage or plants such as maize, wheat, rye, oat, triticale, rice, barley, cotton, manihot, pepper, tagetes, solanaceous plants such as potato, tobacco, eggplant, and tomato, *Vicia* species, pea, alfalfa, bushy plants (coffee, cacao, tea), *Salix* species, trees (oil palm, coconut) and perennial grasses and forage crops. Particularly preferred plants of the invention are oilseed plants such as soybean, peanut, rapeseed, canola, sunflower, safflower, trees (oil palm, coconut).

D. Isolated ASE

Another aspect of the invention pertains to isolated ASEs, and biologically active portions thereof. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of ASE in which the protein is separated from cellular components of the cells in which it is naturally or recombinantly produced. In one embodiment, the language "substantially free of cellular material" includes preparations of ASE having less than about 30% (by dry weight) of non-ASE (also referred to herein as a "contaminating protein"), more preferably less than about 20% of non-ASE, still more preferably less than about 10% of non-ASE, and most preferably less than about 5% of non-ASE. When the ASE or biologically active portion thereof is recombinantly produced, it is also substantially free of culture medium, i.e., culture medium represents less than 20%, more preferably less than 10%, and most preferably less than about 5% of the volume of the protein preparation. The language "substantially free of chemical precursors or other chemicals' includes preparations of ASE in which the protein is separated from chemical precursors or other chemicals which are involved in the synthesis of the protein. In one embodiment, the language "substantially free of chemical precursors or other chemicals" includes preparations of ASE having less than about 30% (by dry weight) of chemical precursors or non-ASE chemicals, more preferably less than about 20% chemical precursors or non-ASE chemicals, still more preferably less than about 10% chemical precursors or non-ASE chemicals, and most preferably less than about 5% chemical precursors or non-ASE chemicals. In preferred embodiments, isolated proteins or biologically active portions thereof lack contaminating proteins from the same organism from which the ASE is derived. Typically, such proteins are produced by recombinant expression of, for example, an *Isochrysis galbana* ASE in other plants than *Isochrysis galbana* or microorganisms such as *C. glutamicum* or ciliates, algae or fungi.

An isolated ASE of the invention or a portion thereof can participate in the metabolism of compounds involved in the construction of cellular membranes in *Isochrysis galbana*, or in the transport of molecules across these membranes, or has one or more of the activities set forth in Tab. 2. In preferred embodiments, the protein or portion thereof comprises an amino acid sequence which is sufficiently homologous to an amino acid sequence of SEQ ID NO: 2 such that the protein or portion thereof maintains the ability to participate in the metabolism of compounds necessary for the construction of cellular membranes in *Isochrysis galbana*, or in the transport of molecules across these membranes. The portion of the protein is preferably a biologically active portion as described herein. In another preferred embodiment, an ASE of the invention has an amino acid sequence shown in SEQ ID NO: 2. In another preferred embodiment, the ASE has an amino acid sequence which is encoded by a nucleotide sequence which hybridizes, e.g., hybridizes under stringent conditions, to a nucleotide sequence of SEQ ID NO: 1. In another preferred embodiment, the ASE has an amino acid sequence which is encoded by a nucleotide sequence that is at least about 50-60%, preferably at least about 60-70%, more preferably at least about 70-80%, 80-90%, 90-95%, and even more preferably at least about 96%, 97%, 98%, 99% or more homologous to one of the amino acid sequences of SEQ ID NO: 2. The preferred ASEs of the present invention also preferably possess at least one of the ASE activities described herein. For example, a preferred ASE of the present invention includes an amino acid sequence encoded by a nucleotide sequence which hybridizes, e.g., hybridizes under stringent conditions, to a nucleotide sequence of SEQ ID NO: 1, and which can participate in the metabolism of compounds necessary for the construction of cellular membranes in *Isochrysis galbana*, or in the transport of molecules across these membranes, or which has one or more of the activities set forth in Tab. 2.

In other embodiments, the ASE is substantially homologous to an amino acid sequence of SEQ ID NO: 2 and retains the functional activity of the protein of one of the sequences of SEQ ID NO: 2 yet differs in amino acid sequence due to natural variation or mutagenesis, as described in detail in subsection I above. Accordingly, in another embodiment, the ASE is a protein which comprises an amino acid sequence which is at least about 50-60%, preferably at least about 60-70%, and more preferably at least about 70-80, 80-90, 90-95%, and most preferably at least about 96%, 97%, 98%, 99% or more homologous to an entire amino acid sequence of SEQUENCE ID NO: 2 and which has at least one of the ASE activities described herein. In another embodiment, the invention pertains to a full *Isochrysis galbana* protein which is substantially homologous to an entire amino acid sequence of SEQ ID NO: 2.

Biologically active portions of an ASE include peptides comprising amino acid sequences derived from the amino acid sequence of an ASE, e.g., the amino acid sequence shown in SEQ ID NO: 2 or the amino acid sequence of a protein homologous to an ASE, which include fewer amino acids than a full length ASE or the full length protein which is homologous to an ASE, and exhibit at least one activity of an ASE. Typically, biologically active portions (peptides, e.g., peptides which are, for example, 5, 10, 15, 20, 30, 35, 36, 37, 38, 39, 40, 50, 100 or more amino acids in length) comprise a domain or motif with at least one activity of an ASE. Moreover, other biologically active portions, in which other regions of the protein are deleted, can be prepared by recombinant techniques and evaluated for one or more of the activities described herein. Preferably, the biologically active portions of an ASE include one or more selected domains/motifs or portions thereof having biological activity.

ASEs are preferably produced by recombinant DNA techniques. For example, a nucleic acid molecule encoding the protein is cloned into an expression vector (as described above), the expression vector is introduced into a host cell (as described above) and the ASE is expressed in the host cell. The ASE can then be isolated from the cells by an appropriate purification scheme using standard protein purification techniques. Alternatively to recombinant expression, an ASE, polypeptide, or peptide can be synthesized chemically using standard peptide synthesis techniques. Moreover, native ASE can be isolated from cells (e.g., endothelial cells), for example using an anti-ASE antibody, which can be produced by standard techniques utilizing an ASE of this invention or fragment thereof.

The invention also provides ASE chimeric or fusion proteins. As used herein, an ASE "chimeric protein" or "fusion protein" comprises an ASE polypeptide operatively linked to a non-ASE polypeptide. An "ASE polypeptide" refers to a polypeptide having an amino acid sequence corresponding to an ASE, whereas a "non-ASE polypeptide" refers to a polypeptide having an amino acid sequence corresponding to a protein which is not substantially homologous to the ASE, e.g., a protein which is different from the ASE and which is derived from the same or a different organism. Within the fusion protein, the term "operatively linked" is intended to indicate that the ASE polypeptide and the non-ASE polypeptide are fused to each other so that both sequences fulfill the predicted function ascribed to the sequence used. The non-ASE polypeptide can be fused to the N-terminus or C-terminus of the ASE polypeptide. For example, in one embodiment the fusion protein is a GST-ASE fusion protein in which the ASE sequences are fused to the C-terminus of the GST sequences. Such fusion proteins can facilitate the purification of recombinant ASEs. In another embodiment, the fusion protein is an ASE containing a heterologous signal sequence at its N-terminus. In certain host cells (e.g., mammalian host cells), expression and/or secretion of an ASE can be increased through use of a heterologous signal sequence.

An ASE chimeric or fusion protein of the invention is produced by standard recombinant DNA techniques. For example, DNA fragments coding for the different polypeptide sequences are ligated together in-frame in accordance with conventional techniques, for example by employing blunt-ended or sticky-ended termini for ligation, restriction enzyme cleavage to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). An ASE-encoding nucleic acid can be cloned into such an expression vector such that the fusion moiety is linked in-frame to the ASE.

Homologs of the ASE can be generated by mutagenesis, e.g., discrete point mutation or truncation of the ASE. As used herein, the term "homolog" refers to a variant form of the ASE which acts as an agonist or antagonist of the activity of the ASE. An agonist of the ASE can retain substantially the same, or a subset, of the biological activities of the ASE. An antagonist of the ASE can inhibit one or more of the activities of the naturally occurring form of the ASE, by, for example, competitively binding to a downstream or upstream member of the cell membrane component metabolic cascade which includes the ASE, or by binding to an ASE which mediates transport of compounds across such membranes, thereby preventing translocation from taking place.

In an alternative embodiment, homologs of the ASE can be identified by screening combinatorial libraries of mutants, e.g., truncation mutants, of the ASE for ASE agonist or antagonist activity. In one embodiment, a variegated library of ASE variants is generated by combinatorial mutagenesis at the nucleic acid level and is encoded by a variegated gene library. A variegated library of ASE variants can be produced by, for example, enzymatically ligating a mixture of synthetic oligonucleotides into gene sequences such that a degenerate set of potential ASE sequences is expressible as individual polypeptides, or, alternatively, as a set of larger fusion proteins (e.g., for phage display) containing the set of ASE sequences therein. There are a variety of methods which can be used to produce libraries of potential ASE homologs from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential ASE sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acid Res. 11:477.

In addition, libraries of fragments of the ASE can be used to generate a variegated population of ASE fragments for screening and subsequent selection of homologs of an ASE. In one embodiment, a library of coding sequence fragments can be generated by treating a double stranded PCR fragment of an ASE coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the ASE.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of ASE homologs. The most widely used techniques, which are amenable to high-throughput analysis, for screening large gene libraries typically include cloning the gene library into replicable expression vectors, transforming appropriate cells with the resulting library of vectors, and expressing the combinatorial genes under conditions in which detection of the desired activity facilitates isolation of the vector encoding the gene whose product was detected. Recursive ensemble mutagenesis (REM), a new technique which enhances the frequency of functional mutants in the libraries, can be used in combination with the screening assays to identify ASE homologs (Arkin and Yourvan (1992) PNAS 89:7811-7815; Delgrave et al. (1993) Protein Engineering 6(3):327-331).

In another embodiment, cell based assays can be exploited to analyze a variegated ASE library, using further methods well known in the art.

E. Uses and Methods of the Invention

The nucleic acid molecules, proteins, protein homologs, fusion proteins, primers, vectors, and host cells described herein can be used in one or more of the following methods: identification of *Isochrysis galbana* and related organisms; mapping of genomes of organisms related to *Isochrysis galbana*; identification and localization of *Isochrysis galbana* sequences of interest; evolutionary studies; determination of ASE regions required for function; modulation of an ASE activity; modulation of the metabolism of one or more cell membrane components; modulation of the transmembrane transport of one or more compounds; and modulation of cellular production of a desired compound, such as a fine chemical, including PUFAs.

The ASE nucleic acid molecules of the invention have a variety of uses. First, they may be used to identify an organism as being *Isochrysis galbana* or a close relative thereof. Also, they may be used to identify the presence of *Isochrysis galbana* or a relative thereof in a mixed population of microorganisms. The invention provides the nucleic acid sequences of a number of *Isochrysis galbana* genes; by probing the extracted genomic DNA of a culture of a unique or mixed population of microorganisms under stringent conditions with a probe spanning a region of an *Isochrysis galbana* gene which is unique to this organism, one can ascertain whether this organism is present. Although *Isochrysis galbana* itself is not used for the commercial production of polyunsaturated acids, algae are the only known plants beside mosses that produce more then a few percent of their total lipids as PUFAs. Therefore DNA sequences related to ASEs are especially suited to be used for PUFA production in other organisms.

Further, the nucleic acid molecules and protein molecules of the invention may serve as markers for specific regions of the genome. This has utility not only in the mapping of the genome, but also for functional studies of *Isochrysis galbana* proteins. For example, to identify the region of the genome to which a particular *Isochrysis galbana* DNA-binding protein binds, the *Isochrysis galbana* genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment on the genome map of *Isochrysis galbana*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map for related algae, such as *Isochrysis galbana*.

The ASE nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the ASE nucleic acid molecules of the invention may result in the production of ASEs having functional differences from the wild-type ASEs. These proteins may be improved in efficiency or activity, may be present in greater numbers in the cell than is usual, or may be decreased in efficiency or activity. Improved efficiency or activity means for example the enzyme has a higher selectivity and/or activity than the original enzyme, preferably at least 10% higher, particularly preferably at least 20% higher activity, most particularly preferably at least 30% higher activity.

There are a number of mechanisms by which the alteration of an ASE of the invention may directly affect the yield, production, and/or efficiency of production of a fine chemical incorporating such an altered protein. Recovery of fine chemical compounds from large-scale cultures of ciliates, algae or fungi is significantly improved if the cell secretes the desired compounds, since such compounds may be readily isolated from the culture medium (as opposed to extracted from the mass of cultured cells). Otherwise purification can be improved if preferably the cell stores compounds in a specialized compartment having a kind of concentrating mechanism in vivo. In the case of plants expressing ASEs increased transport can lead to improved partitioning within the plant tissue and organs. By either increasing the number or the activity of transporter molecules which export fine chemicals from the cell, it may be possible to increase the amount of the produced fine chemical which is present in the extracellular medium, thus permitting greater ease of harvesting and purification or, in the case of plants, more efficient partitioning. Conversely, in order to efficiently overproduce one or more fine chemicals, increased amounts of the cofactors, precursor molecules, and intermediate compounds for the appropriate biosynthetic pathways are required. By increasing the number and/or activity of transporter proteins involved in the import of nutrients, such as carbon sources (i.e., sugars), nitrogen sources (i.e., amino acids, ammonium salts), phosphate, and sulfur, it may be possible to improve the production of a fine chemical, due to the removal of any nutrient supply limitations on the biosynthetic process. Fatty acids such as PUFAs and lipids containing PUFAs are themselves desirable fine chemicals, so by optimizing the activity or increasing the number of one or more ASEs of the invention which participate in the biosynthesis of these compounds, or by impairing the activity of one or more genes which are involved in the degradation of these compounds, it may be possible to increase the yield, production, and/or efficiency of production of fatty acid and lipid molecules in ciliates, algae, plants, fungi, yeasts or other microorganisms.

The engineering of one or more ASE genes of the invention may also result in ASEs having altered activities which indirectly impact the production of one or more desired fine chemicals from algae, plants, ciliates or fungi. For example, the normal chemical processes of metabolism result in the production of a variety of waste products (e.g., hydrogen peroxide and other reactive oxygen species) which may actively interfere with these same metabolic processes (for example, peroxynitrite is known to nitrate tyrosine side chains, thereby inactivating some enzymes having tyrosine in the active site (Groves, J. T. (1999) *Curr. Opin. Chem. Biol.* 3(2): 226-235). While these waste products are typically excreted, cells utilized for large-scale fermentative production are optimized for the overproduction of one or more fine chemicals, and thus may produce more waste products than is typical for a wild-type cell. By optimizing the activity of one or more ASEs of the invention, it may be possible to improve the viability of the cell and to maintain efficient metabolic activity, thereby improving the production of the desired product such as PUFAs. Also, the presence of high intracellular levels of the desired fine chemical may actually be toxic to the cell, so by increasing the ability of the cell to secrete these compounds, one may further improve the viability of the cell.

Further, the ASEs of the invention may be manipulated such that the relative amounts of various lipid and fatty acid molecules are altered. This may have a profound effect on the lipid composition of the membrane of the cell. Since each type of lipid has different physical properties, an alteration in the lipid composition of a membrane may significantly alter membrane fluidity. Changes in membrane fluidity can impact the transport of molecules across the membrane, which, as previously explicated, may modify the export of waste products or the produced fine chemical or the import of necessary nutrients. Such membrane fluidity changes may also profoundly affect the integrity of the cell; cells with relatively weaker membranes are more susceptible to abiotic and biotic stress conditions which may damage or kill the cell. By manipulating ASEs involved in the production of fatty acids and lipids for membrane construction such that the resulting membrane has a membrane composition more amenable to the environmental conditions extant in the cultures utilized to produce fine chemicals, a greater proportion of the cells should survive and multiply. Greater numbers of producing cells should translate into greater yields, production, or efficiency of production of the fine chemical from the culture.

The aforementioned mutagenesis strategies for ASEs to result in increased yields of a fine chemical are not meant to be limiting; variations of these strategies will be readily apparent to one skilled in the art. Using such strategies, and incorporating the mechanisms disclosed herein, the nucleic acid molecules and protein molecules of the invention may be utilized to generate algae, ciliates, plants, animals, fungi or other microorganisms like *C. glutamicum* expressing mutated ASE nucleic acid and protein molecules such that the yield, production, and/or efficiency of production of a desired compound is improved. This desired compound may be any natural product of algae, ciliates, plants, animals or fungi, which includes the final products of biosynthesis pathways and intermediates of naturally-occurring metabolic pathways, as well as molecules which do not naturally occur in the metabolism of said cells, but which are produced by the cells of the invention.

Another embodiment of the invention is a method for production of PUFAs, said method comprising growing an organism which comprises a nucleic acid of the invention, a gene construct of the invention or a vector of the invention which encodes a polypeptide which elongates α-linolenic acid ($C_{18:3}$ $\Delta 9, 12, 15$) by at least two carbon atoms but not γ-linolenic acid ($C_{18:3\ \Delta6,\ 9,\ 12}$), under conditions whereby PUFAs are produced in said organism. Preferably the method comprises the growing of an organism which comprises a nucleotide sequence which encodes a polypeptide which elongates α-linolenic acid ($C_{18:3\ \Delta9,\ 12,\ 15}$) by at least two carbon atoms whereas γ-linolenic acid ($C_{18:3\ \Delta6,\ 9,\ 12}$) is not elongated, selected from the group consisting of
a) a nucleic acid sequence depicted in SEQ ID NO: 1,
b) a nucleic acid sequence which encodes a polypeptide depicted in SEQ ID NO: 2,
c) derivatives of the sequence depicted in SEQ ID NO: 1, which encodes polypeptides having at least 50% homology to the sequence encoding amino acid sequences depicted in SEQ ID NO: 2 and which sequences function as an elongase.

More preferably the nucleic acid sequence is derived from a plant, preferably from the genus *Isochrysis*. The used sequence codes for a polypeptide which elongates Δ9 fatty acids.

The PUFAs produced by this method are preferably $C_{20}$ or $C_{22}$ fatty acid molecules having at least two double bonds in the fatty acid molecule, preferably at least three double bonds.

Organisms which are useful in the inventive method for the production of PUFAs are microorganism such as bacteria like Gram-positive or G@@@@ram-negative bacteria or preferably blue algae, ciliates such as *Colpidium* or *Stylonichia*, fungi such as *Mortierella* or *Thraustochytrium* or *Schizochytrium*, algae such as *Phaeodactylum*, and/or plants like maize, wheat, rye, oats, triticale, rice, barley, soybean, peanut, cotton, *Brassica* species like rapeseed, canola and turnip rape, linseed, pepper, sunflower, borage, evening primrose and tagetes, solanaceous plants like potato, tobacco, eggplant, and tomato, *Vicia* species, pea, manihot, alfalfa, bushy plants (coffee, cacao, tea), *Salix* species, trees (oil palm, coconut) and perennial grasses and forage crops, either directly, e.g., mosses or other plants where overexpression or optimization of a fatty acid biosynthesis protein has a direct impact on the yield, production, and/or efficiency of production of the fatty acid from modified organisms.

PUFAs can be produced in the inventive process in the form of an oil, lipid or free fatty acid. PUFAs produced by this method can be isolated by harvesting the organisms either from the culture in which they were growing or from the field, disrupting and/or extracting the harvested material with an organic solvent. From said solvent the oil containing lipids, phospholipids, sphingolipids, glycolipids, triacylglycerols and/or free fatty acids with a higher content of PUFAs can be isolated. By basic or acid hydrolysis of the lipids, phospholipids, sphingolipids, glycolipids or triacylglycerols, the free fatty acids with a higher content of PUFAs can be isolated. Higher content of PUFAs means at least 1%, preferably 10%, particularly preferably 20%, most particularly preferably 40% more PUFAs than the original organism which has no additional nucleic acid coding for the inventive elongase.

Besides the abovementioned methods, plant lipids are extracted preferably from plant material as described by Cahoon et al. (1999) PNAS 96 (22): 12935-12940 and Browse et al. (1986) Analytic Biochemistry 152: 141-145. Qualitative and quantitative lipid or fatty acid analysis is described in Christie, William W., Advances in Lipid Methodology, Ayr/Scotland: Oily Press. —(Oily Press Lipid Library; 2); Christie, William W., Gas Chromatography and Lipids. A Practical Guide—Ayr, Scotland: Oily Press, 1989 Repr. 1992—IX, 307 p. —(Oily Press Lipid Library; 1); "Progress in Lipid Research, Oxford: Pergamon Press, 1(1952)-16(1977) under the title: Progress in the Chemistry of Fats and Other Lipids.

PUFAs produced by this method are preferably $C_{20}$ or $C_{22}$ fatty acid molecules having at least two double bonds in the fatty acid molecule, preferably three to four double bonds, particularly preferably three double bonds. Such $C_{20}$ or $C_{22}$ fatty acid molecules can be isolated from the organism in the form of an oil, lipid or free fatty acid. Organisms which are useful are for example the ones mentioned above. Preferred organisms are transgenic plants.

One embodiment of the invention is oils, lipids or fatty acids or fractions thereof produced by the method described above, particularly preferably an oil, lipid or fatty acid composition comprising PUFAs derived from transgenic plants.

A further embodiment of the invention is the use of said oil, lipid or fatty acid composition in feed, food, cosmetics or pharmaceuticals.

An additional embodiment of the invention is a monoclonal or polyclonal antibody which specifically interacts with a polypeptide encoded by the inventive nucleic acid sequence described above and which is produced by a method known by the skilled worker.

A further embodiment of the invention is a kit comprising an inventive nucleotide sequence, a gene construct as claimed, a vector as claimed or an antibody as described above. Said kit is useful for example for the identification of the protein, the nucleic acid sequence.

The aforementioned mutagenesis strategies for ASEs to result in increased yields of a fine chemical are not meant to be limiting; variations on these strategies will be readily apparent to one skilled in the art. Using such strategies, and incorporating the mechanisms disclosed herein, the nucleic acid molecules and protein molecules of the invention may be utilized to generate algae, ciliates, plants, fungi or other microorganisms like *C. glutamicum* expressing mutated ASE nucleic acid and protein molecules such that the yield, production, and/or efficiency of production of a desired compound is improved. This desired compound may be any natural product of algae, ciliates, plants, fungi or *C. glutamicum*, which includes the final products of biosynthesis pathways and intermediates of naturally-occurring metabolic pathways, as well as molecules which do not naturally occur in the metabolism of said cells, but which are produced by said cells of the invention.

This invention is further illustrated by the following examples which should not be construed as limiting. The contents of all references, patent applications, patents, and published patent applications cited throughout this application are hereby incorporated by reference.

EXAMPLES

Example 1

General Processes a) Cloning Processes and General Methods

Cloning processes such as, for example, restriction cleavages, agarose gel electrophoresis, purification of DNA fragments, transfer of nucleic acids to nitrocellulose and nylon membranes, linkage of DNA fragments, transformation of *Escherichia coli* and yeast cells, growth of bacteria and sequence analysis of recombinant DNA were carried out as described in Sambrook et al. (1989) (Cold Spring Harbor Laboratory Press: ISBN 0-87969-309-6) or Kaiser, Michaelis and Mitchell (1994) "Methods in Yeast Genetics" (Cold Spring Harbor Laboratory Press: ISBN 0-87969-451-3). Transformation and cultivation of algae such as *Chlorella* or

*Phaeodactylum* are performed as described by El-Sheekh (1999), Biologia Plantarum 42: 209-216; Apt et al. (1996), Molecular and General Genetics 252 (5): 872-9.

b) Chemicals:

The chemicals used were obtained, if not mentioned otherwise in the text, in p.a. quality from the companies Fluka (Neu-Ulm), Merck (Darmstadt), Roth (Karlsruhe), Serva (Heidelberg) and Sigma (Deisenhofen). Solutions were prepared using purified, pyrogen-free water, designated as $H_2O$ in the following text, from a Milli-Q water system water purification plant (Millipore, Eschborn). Restriction endonucleases, DNA-modifying enzymes and molecular biology kits were obtained from the companies AGS (Heidelberg), Amersham (Braunschweig), Biometra (Göttingen), Boehringer (Mannheim), Genomed (Bad Oeynhausen), New England Biolabs (Schwalbach/Taunus), Novagen (Madison, Wis., USA), Perkin-Elmer (Weiterstadt), Pharmacia (Freiburg), Qiagen (Hilden) and Stratagene (Amsterdam, Netherlands). They were used, if not mentioned otherwise, according to the manufacturer's instructions.

c) Algal Material

For this study, algae of the species *Isochrysis galbana* CCAP 927/1 were used, obtained from the Culture Collection of Algae and Protozoa, Centre for Coastal and Marine Sciences, Dunstaffnage Marine Laboratory, Oban, Argyll; UK.

Cultivation of Algae

*Isochrysis galbana* was cultured using the f/2 medium containing 10% organic medium as described by Guillard, R. R. L. [1975; Culture of phytoplankton for feeding marine invertebrates. In: Smith, W. L. and Chanley, M. H. (Eds.) Culture of marine Invertebrate animals, NY Plenum Press, pp. 29-60.]. *Isochrysis galbana* was cultured at 14° C. under continuous light and a light intensity of 30 microEinstein in glass vessels with shaking at 100 rpm.

The f/2 medium consists of:

995.5 ml artificial sea water containing:

1 ml $NaNO_3$ (75 g/l), 1 ml $NaH_2PO_4$ (5 g/l), 1 ml trace element solution, 1 ml Tris/Cl pH 8.0, 0.5 ml f/2 vitamin solution Trace element solution:

$Na_2EDTA$ (4.36 g/l), $FeCl_3$ (3.15 g/l),

Primary trace elements:

$CuSO_4$ (10 g/l), $ZnSO_4$ (22 g/l), $CoCl_2$ (10 g/l), $MnCl_2$ (18 g/l), $NaMoO_4$ (6.3 g/l)

f/2 vitamin solution:

biotin: 10 mg/l, thiamine 200 mg/l, vit B12 0.1 mg/l

Org. Medium:

Na acetate (1 g/l), glucose (6 g/l),

Na succinate (3 g/l),

Bacto-Tryptone (4 g/l),

Yeast extract (2 g/l)

Example 2

DNA Isolation from Algae

The details for the isolation of total DNA relate to the working up of one gram fresh weight of material harvested by filtration.

CTAB Buffer:

2% (w/v) N-cetyl-N,N,N-trimethylammonium bromide (CTAB);

100 mM Tris HCl pH 8.0;

1.4 M NaCl;

20 mM EDTA.

N-Laurylsarcosine Buffer:

10% (w/v) N-laurylsarcosine;

100 mM Tris HCl pH 8.0;

20 mM EDTA.

The material was homogenized under liquid nitrogen with quartz sand in a mortar to give a fine powder and transferred to 2 ml Eppendorf cups. The frozen material was then covered with a layer of 1 ml of decomposition buffer (1 ml CTAB buffer, 100 ml of N-laurylsarcosine buffer, 20 ml of beta-mercaptoethanol and 10 ml of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 min in each case. The DNA was then precipitated at 70° C. for 30 min. The precipitated DNA was sedimented at 4° C. and 10,000 g for 30 min and resuspended in 100 microliters of TE buffer (Sambrook et al., 1989, Cold Spring Harbor Laboratory Press: ISBN 0-87969-309-6). For further purification, the DNA was treated with NaCl (1.2 M final concentration) and precipitated again at 70° C. for 30 min using twice the volume of absolute ethanol. After a washing step with 70% ethanol, the DNA was dried and subsequently taken up in 50 microliters of $H_2O$+DNase free RNase (50 mg/ml final concentration). The DNA was dissolved overnight at 4° C. and the RNase digestion was subsequently carried out at 37° C. for 1 h. Storage of the DNA took place at 4° C.

Example 3

Isolation of Total RNA and Poly(A)+RNA from Algae

For the investigation of transcripts, both total RNA and poly(A)+RNA were isolated.

Algal cultures were harvested by centrifugation at 3000 g for 5 minutes. The pellets were immediately frozen in liquid nitrogen (−70° C.). Algal material (1 g) was homogenized with a pestle in a mortar under liquid nitrogen. The material was desintegrated to homogeneity in two volumes of buffer which was TriPure™ Isolation Reagent (Roche). The total RNA was then isolated following the manufacturer's protocol.

Isolation of Poly(A)+RNA was carried out using Amersham Pharmacia mRNA Isolation Kit following the instructions of the manufacturer's protocol.

After determination of the concentration of the RNA or of the poly(A)+RNA, the RNA was precipitated by addition of 1/10 volumes of 3 M sodium acetate pH 4.6 and 2 volumes of ethanol and stored at −70° C.

Example 4 cDNA Library Construction

Double stranded cDNA was synthesised using the cDNA Synthesis Kit from Stratagene following the manufacturer's protocol. It was then passed through a Sephacyl S-400 Spun Column from a cDNA Synthesis Kit (Amersham Pharmacia) to remove adapters and smaller molecules. cDNA eluted from the column was phenol extracted, ethanol precipitated and ligated to the arms of the Uni-Zap vector and packed into λ phages using Ready-To-Go Lambda Packaging Kit (Amersham Pharmacia Biotech) following the manufacturer's instructions. A library of 1×10$^6$ pfu was obtained with the majority of the inserts ranging from 0.4-2 kb.

Example 5

Identification of the ASE1 Gene and Analysis of the cDNA-clone Ig_ASE1

From an alignment of known elongase sequences (from *M. alpina*, *S. cerevisiae* (Elo1, Elo2, Elo3), *C. elegans* (F56H11.4, F41H10.8)) the common motif MYXYYFL (SEQ ID NO:3) was chosen for oligonucleotide design.

The reverse complement oligo

5'-AAAAAATAATAIIIGTACAT-3' (SEQ ID NO:4)

5'-AGGAAGTAGTAIIIATACAT-3'    (SEQ ID NO:5)
(I=deoxyinosine)

was synthesised and used in touchdown PCR with a universal T3 promoter primer (5'-AATTAACCCTCACTAAAGGG-3') (SEQ ID NO:6) using an *Isochrysis galbana* cDNA library as template.

The PCR conditions were:

94° C. for 3 min (1 cycle)

94° C. for 15 sec, 52° C. for 30 sec, 72° C. for 45 sec (4 cycles)

94° C. for 15 sec, 52° C. for 30 sec (with 1° C. decrement every cycle),

72° C. for 45 sec (10 cycles)

94° C. for 15 sec, 42° C. for 30 sec, 72° C. for 45 sec (25 cycles)

72° C. for 6 min (1 cycle).

A PCR product of about 650 bp was cloned and sequenced and the deduced amino acid sequence was found to align with the putative elongase sequence compilation. The gene-specific (sense) primer

5'-ACTCGAAGCTCTTCACATGG-3 (SEQ ID NO: 7)

was synthesised and used in a further library PCR reaction with a universal M13 forward primer (5'-GTAAAACGACGGCCAGT-3') (SEQ ID NO:8)

using the following conditions:

94° C. for 3 min (1 cycle)

94° C. for 15 sec, 55° C. for 30 sec, 72° C. for [lacuna] (10 cycles)

94° C. for 15 sec, 55° C. for 30 sec, 72° C. for 1 min 33 sec (with 3 sec increment every cycle) (20 cycles)

72° C. for 6 min (1 cycle).

A PCR product of about 850 bp was cloned and sequenced. The two PCR product sequences overlapped, confirming that they were ultimately derived from a single gene.

Those cDNA clones isolated from cDNA libraries as described in Example 6 were used for DNA sequencing according to standard methods, in particular by the chain termination method using the ABI PRISM Big Dye Terminator Cycle Sequencing Ready Reaction Kit (Perkin-Elmer, Weiterstadt, Germany). Sequencing was carried out subsequent to plasmid recovery from cDNA libraries via in vivo excision and retransformation of DH10$_B$ on agar plates (material and protocol details from Stratagene, Amsterdam, Netherlands).

Plasmid DNA was prepared from overnight grown *E. coli* cultures grown in Luria-Broth medium containing ampicillin [see Sambrook et al. (1989) (Cold Spring Harbor Laboratory Press: ISBN 0-87969-309-6)].

Sequencing primers with the following nucleotide sequences were used:

5'-CAGGAAACAGCTATGACC-3'    (SEQ ID NO:9)

5'-CTAAAGGGAACAAAAGCTG-3'   (SEQ ID NO:11)

5'-TGTAAAACGACGGCCAGT-3'    (SEQ ID NO:11)

The complete nucleotide sequence of the cDNA consisted of about 1064 bp. It contained an open reading frame of 789 bp encoding 263 amino acids. The protein sequence shares just low identity or similarity with known genes such elongases which are required for medium-chain-length fatty acid elongation in yeast (Toke & Martin, 1996, Isolation and characterization of a gene affecting fatty acid elongation in *Saccharomyces cerevisiae*. Journal of Biological Chemistry 271, 18413-18422.).

TABLE 1

Alignment of *Isochrysis galbana* elongase with homologous sequences.

| Gene | M. alpina | Human | Mouse | Yeast | C. elegans |
|---|---|---|---|---|---|
| Ig_ASE1 | 27 | 25.5[1] 20.2[2] | 24.3 | 21[3] 23.2[4] 23.6[5] | 19 |

The values in the table are percentage identities from pairwise alignment using DNAMAN (Lynnon Biosoft). Parameters used: Matrix: BLOSUM, Alignment method: optimal K-tuple: 2, Gap open: 10, Gap penalty: 4, Gap extension: 0.1;
[1]= ELOVL4;
[2]= Helo1;
[3]= Elo1;
[4]= Elo2;
[5]= Elo3.

The sequences have been taken from human ELOVL (article 1, sequence 1), human Helo1 (article 1, sequence 2), *M. alpina* (Glelo, article 3), *C. elegans* (article 4), mouse Elovl4 (article 1), yeast (sequence 3, 4, 5 from articles 5 and 6).

1. Zhang et al., Nature Gen. 27: 89-93 (2001)
2. Leonard et al., Biochem. J. 350: 765-770 (2000).
3. Parker-Barnes et al., Proc. Natl. Sci. USA 97: 8284-8289, (2000).
4. Beaudoin et al., Proc Natl. Sci. USA 97: 6421-6426. (2000)
5. Toke and Martin, J. Biol. Chem. 271: 18413-18422 (1996)
6. Oh et al., J. Biol. Chem. 272: 17373-17384 (1997).

Pairwise alignments of the Ig_ASE1 gene and *Mortierella* and mouse homologs are shown in FIG. 1 and FIG. 2.

The following parameters were used for the alignments:

| | |
|---|---|
| Pairwise alignments: | Fixed penalty: 10 |
| Ktuple: 1 | Floating penalty: 10 |
| Number of diagonals: 3 | Window size: 5 |
| Weight matrix (protein): PAM 250 | Gap penalty: 5 |

Example 6

Identification of Genes by Hybridization

Gene sequences can be used to identify homologous or heterologous genes from cDNA or genomic libraries.

Homologous genes (e.g. full length cDNA clones homologous to [lacuna] and homologs) can be isolated via nucleic acid hybridization using for example cDNA libraries: Depending on the abundance of the gene of interest 100 000 up to 1 000 000 recombinant bacteriophages are plated and transferred to a nylon membrane. After denaturation with alkali, DNA is immobilized on the membrane by e.g. UV crosslinking. Hybridization is carried out at high stringency conditions. In aqueous solution hybridization and washing are performed at an ionic strength of 1 M NaCl and a temperature of 68° C. Hybridization probes are generated by e.g. radioactive ($^{32}$P) nick transcription labeling (High Prime, Roche, Mannheim, Germany). Signals are detected by autoradiography.

Partially homologous or heterologous genes that are related but not identical can be identified analogously to the above described procedure using low stringency hybridization and washing conditions. For aqueous hybridization the ionic strength is normally kept at 1 M NaCl while the temperature is progressively lowered from 68 to 42° C.

Isolation of gene sequences with homologies only in a distinct domain of (for example) 10-20 amino acids can be carried out by using synthetic radiolabeled oligonucleotide probes. Radio-labeled oligonucleotides are prepared by phosphorylation of the 5'-end of two complementary oligonucleotides with T4 polynucleotide kinase. The complementary oligonucleotides are annealed and ligated to form concatemers. The double stranded concatemers are than radiolabled by for example nick transcription. Hybridization is normally performed at low stringency conditions using high oligonucleotide concentrations.

Oligonucleotide hybridization solution:

6× SSC 0.01 M sodium phosphate 1 mM EDTA (pH 8)

0.5% SDS

100 µg/ml denaturated salmon sperm DNA 0.1% nonfat dried milk

During hybridization temperature is lowered stepwise to 5-10° C. below the estimated oligonucleotide Tm or down to room temperature followed by washing steps and autoradiography. Washing is performed with extremely low stringency such as 3 washing steps using 4× SSC. Further details are described by Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons.

Example 7

Plasmids for Plant Transformation

For plant transformation binary vectors such as pGPTV (Becker et al. 1992, Plant Mol. Biol. 20:1195-1197) or pBinAR can be used (Höfgen and Willmitzer, Plant Science 66 (1990), 221-230). Construction of the binary vectors can be performed by ligation of the cDNA in sense or antisense orientation into the T-DNA. 5' to the cDNA a plant promotor activates transcription of the cDNA. A polyadenylation sequence is located 3' to the cDNA.

Tissue specific expression can be achieved by using a tissue specific promotor. For example seed specific expression can be achieved by cloning the DC3 or LeB4 or USP promotor 5' to the cDNA. Also any other seed specific promotor element can be used. For constitutive expression within the whole plant the CaMV 35S promotor can be used.

The expressed protein can be targeted to a cellular compartment using a signal peptide, for example for plastids, mitochondria or endoplasmatic reticulum (Kermode, Crit. Rev. Plant Sci. 15, 4 (1996), 285-423). The signal peptide is cloned 5' in frame to the cDNA to achieve subcellular localization of the fusion protein.

Example 8

Transformation of *Agrobacterium*

*Agrobacterium* mediated plant transformation can be performed using for example *Agrobacterium* strain C58C1 pGV2260 (Deblaere et al. 1984, Nucl. Acids Res. 13, 4777-4788) or GV3101(pMP90) (Koncz and Schell, Mol. Gen. Genet. 204 (1986), 383-396) or LBA 4404 (Clontech). Transformation can be performed by standard transformation techniques (Deblaere et al., Nucl. Acids. Res. 13 (1984), 4777-4788).

Example 9

Plant Transformation

*Agrobacterium* mediated plant transformation can be performed using standard transformation and regeneration techniques (Gelvin, Stanton B.; Schilperoort, Robert A, Plant Molecular Biology Manual, 2nd Ed. —Dordrecht: Kluwer Academic Publ., 1995. ISBN 0-7923-2731-4; Glick, Bernard R.; Thompson, John E., Methods in Plant Molecular Biology and Biotechnology, Boca Raton: CRC Press, 1993. —360 pp., ISBN 0-8493-5164-2).

For example rapeseed can be transformed via cotyledon or hypocotyl transformation (Moloney et al., Plant cell Report 8 (1989), 238-242; De Block et al., Plant Physiol. 91 (1989), 694-701). Use of antibiotics for *agrobacterium* and plant selection depends on the binary vector and the agrobacterium strain used for transformation. Rapeseed selection is normally performed using kanamycin as selectable plant marker.

*Agrobacterium* mediated gene transfer to flax can be performed using for example a technique described by Mlynarova et al. (1994), Plant Cell Report 13: 282-285.

Transformation of soybean can be performed using for example a technique described in EP 0424 047, U.S. Pat. No. 322,783 (Pioneer Hi-Bred International) or in EP 0397 687, U.S. Pat. No. 5,376,543, U.S. Pat. No. 5,169,770 (University Toledo).

Plant transformation using particle bombardment, polyethylene glycol mediated DNA uptake or via the silicon carbide fiber technique is for example described by Freeling and Walbot in: "The maize handbook" (1993) ISBN 3-540-97826-7, Springer Verlag New York.

Example 10

In Vivo Mutagenesis

In vivo mutagenesis of microorganisms can be performed by passage of plasmid (or other vector) DNA through *E. coli* or other microorganisms (e.g. *Bacillus* spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D. (1996) DNA repair mechanisms, in: *Escherichia coli* and *Salmonella*, p. 2277-2294, ASM: Washington). Such strains are well known to those skilled in the art. The use of such strains is illustrated, for example, in Greener, A. and Callahan, M. (1994) Strategies 7: 32-34. Transfer of mutated DNA molecules into plants is preferably done after selection and testing in microorganisms. Transgenic plants are generated according to various examples within the Examples section of this document.

Example 11

Assessment of the Expression of a Recombinant Gene Product in a Transformed Organism The activity of a recombinant gene product in the transformed host organism has been measured on the transcriptional and/or on the translational level.

A useful method to ascertain the level of transcription of the gene (an indicator of the amount of mRNA available for translation of the gene product) is to perform a Northern blot (for reference see, for example, Ausubel et al. (1988) Current Protocols in Molecular Biology, Wiley: New York or within the abovementioned Examples section), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information is evidence of the degree of transcription of the transformed gene. Total cellular RNA can be prepared from cells, tissues or organs by several methods, all well-known in the art, such as that described in Bormann, E. R. et al. (1992) *Mol. Microbiol.* 6: 317-326.

To assess the presence or relative quantity of protein translated from this mRNA, standard techniques, such as a Western blot, may be employed (see, for example, Ausubel et al. (1988) Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or calorimetric label which may be readily detected. The presence and quantity of label observed indicates the presence and quantity of the desired mutant protein present in the cell.

Example 12

Analysis of Impact of Recombinant Proteins on the Production of the Desired Product The effect of the genetic modification in plants, fungi, algae, ciliates or [lacuna] on production of a desired compound (such as fatty acids) can be assessed by growing the modified microorganisms or plants under suitable conditions (such as those described above) and analyzing the medium and/or the cellular component for increased production of the desired product (i.e., lipids or a fatty acid). Such analysis techniques are well known to one skilled in the art, and include spectroscopy, thin layer chromatography, staining methods of various kinds, enzymatic and microbiological methods, and analytical chromatography such as high performance liquid chromatography (see, for example, Ullmann, Encyclopedia of Industrial Chemistry, vol. A2, p. 89-90 and p. 443-613, VCH: Weinheim (1985); Fallon, A. et al., (1987) Applications of HPLC in Biochemistry in: Laboratory Techniques in Biochemistry and Molecular Biology, vol. 17; Rehm et al. (1993) Biotechnology, vol. 3, Chapter III: Product recovery and purification, pages 469-714, VCH: Weinheim; Belter, P. A. et al. (1988) Bioseparations: downstream processing for biotechnology, John Wiley and Sons; Kennedy, J. F. and Cabral, J. M. S. (1992) Recovery processes for biological materials, John Wiley and Sons; Shaeiwitz, J. A. and Henry, J. D. (1988) Biochemical separations, in: Ullmann's Encyclopedia of Industrial Chemistry, vol. B3, Chapter 11, pages 1-27, VCH: Weinheim; and Dechow, F. J. (1989) Separation and purification techniques in biotechnology, Noyes Publications.).

Besides the abovementioned methods, plant lipids are extracted from plant material as described by Cahoon et al. (1999) PNAS 96 (22): 12935-12940 and Browse et al. (1986) Analytic Biochemistry 152: 141-145. Qualitative and quantitative lipid or fatty acid analysis is described by Christie, William W., Advances in Lipid Methodology, Ayr/Scotland: Oily Press. —(Oily Press Lipid Library; 2); Christie, William W., Gas Chromatography and Lipids. A Practical Guide— Ayr, Scotland: Oily Press, 1989 Repr. 1992. —IX, 307 pages—(Oily Press Lipid Library; 1); "Progress in Lipid Research, Oxford: Pergamon Press, 1(1952)—16(1977) under the title: Progress in the Chemistry of Fats and Other Lipids.

In addition to the measurement of the final product of fermentation, it is also possible to analyze other components of the metabolic pathways utilized for the production of the desired compound, such as intermediates and by-products, to determine the overall efficiency of production of the compound. Analysis methods include measurements of nutrient levels in the medium (e.g., sugars, hydrocarbons, nitrogen sources, phosphates, and other ions), measurements of biomass composition and growth, analysis of the production of common metabolites of biosynthetic pathways, and measurement of gases produced during fermentation. Standard methods for these measurements are outlined in Applied Microbial Physiology, A Practical Approach, P. M. Rhodes and P. F. Stanbury, eds., IRL Press, p. 103-129; 131-163; and 165-192 (ISBN: 0199635773) and references cited therein.

One example is the analysis of fatty acids (abbreviations: FAME, fatty acid methyl ester; GC-MS, gas-liquid chromatography-mass spectrometry; TAG, triacylglycerol; TLC, thin-layer chromatography).

Unequivocal proof for the presence of fatty acid products can be obtained by the analysis of recombinant organisms following standard analytical procedures: GC, GC-MS or TLC as variously described by Christie and references therein (1997, in: Advances on Lipid Methodology—Fourth ed.: Christie, Oily Press, Dundee, 119-169; 1998, gas-chromatography-mass spectrometry methods, Lipids 33:343-353).

Material to be analyzed can be disintegrated via sonification, glass milling, liquid nitrogen and grinding or via other applicable methods. The material has to be centrifuged after disintegration. The sediment is resuspended in Aqua dest, heated for 10 min at 100° C., cooled on ice and centrifuged followed by extraction in 0.5 M sulfuric acid in methanol containing 2% dimethoxypropane for 1 h at 90° C., leading to hydrolyzed oil and lipid compounds resulting in transmethylated lipids. These fatty acid methyl esters are extracted in petroleum ether and finally subjected to GC analysis using a capillary column (Chrompack, WCOT Fused Silica, CP-Wax-52 CB, 25 m, 0.32 mm) at a temperature gradient between 170° C. and 240° C. for 20 min and 5 min at 240° C. The identity of the resulting fatty acid methyl esters has to be defined by the use of standards available form commercial sources (i.e. Sigma).

In the case of fatty acids where standards are not available molecule identity has to be shown via derivatization and subsequent GC analysis. For example the localization of triple bond fatty acids has to be shown via GC-MS after derivatization with 4,4-dimethoxyoxazoline derivatives (Christie, 1998, see above).

Example 13

Expression Products in Heterologous Microbial Systems

Strains, Growth Conditions and Plasmids

*Escherichia coli* strain XL1 Blue MRF' kan (Stratagene) was used for subcloning the new elongase Ig_ASE1 from *Isochrysis galbana*. For functional expression of this gene we used the *Saccharomyces cerevisiae* strain INVSc 1 (Invitrogen Co.). *E. coli* was grown in Luria-Bertani broth (LB, Duchefa, Haarlem, The Netherlands) at 37° C. When neccessary, ampicillin (100 mg/liter) was added and 1.5% (w/v) agar (Difco) was included for solid LB media. *S. cerevisiae* was grown at 30° C. either in YPG-medium or in complete minimal dropout uracil medium (CMdum; see in: Ausubel, F. M., Brent, R., Kingston, R. E., Moore, D. D., Seidman, J. G., Smith, J. A., Struhl, K., Albright, L. B., Coen, D. M., and Varki, A. (1995), Current Protocols in Molecular Biology, John Wiley & Sons, New York.) containing either 2% (w/v) raffinose or glucose. For solid media 2% (w/v) Bacto™ agar (Difco) was included. Plasmids used for cloning and expression were pUC 18 (Pharmacia) and pYES2 (Invitrogen Co.).

Example 14

Cloning and Expression of an ALA-PUFA Specific Elongase (ASE Gene) from *Isochrysis Galbana* in Yeast a) Cloning Procedures For expression in yeast, the *Isochrysis galbana* gene Ig_ASE1 was first modified to create restriction sites and the yeast consensus sequence for highly efficient translation (Kozak, M. (1986). Point mutations define a sequence flanking the AUG initiator codon that modulates translation by eukaryotic ribosomes (*Cell* 44, 283-292.). A site adjacent to the start codon was introduced. For amplification of the open reading frame a pair of primers complementary to its 5'- and 3'-end were synthesized.

```
                                          (SEQ ID NO:12)
Forward primer:    5'-GGTACCATGGCCCTCGCAAACGA-3'

(SEQ ID NO:13)
Reverse primer:    5'-TAGGACATCCACAATCCAT-3'
```

The PCR reaction was performed with plasmid-DNA as template in a Thermocycler (Biometra) using Pfu DNA polymerase (Stratagene) and the following temperature program: 3 min. at 96° C. followed by 25 cycles with 30 s at 96° C., 30 s at 55° C. and 3 min. at 72° C., 1 cycle with 10 min. at 72° C. and stop at 4° C.

The correct size of the amplified DNA fragment of about 800 bp was confirmed by Agarose-TBE gel electrophoresis. The amplified DNA was extracted from the gel with the QIAquick Gel Extraktion Kit (QIAGEN) and ligated into the T/A-site of the vector pCR 21 (Invitrogen) using the Sure Clone Ligation Kit (Pharmacia). After transformation of *E. coli* XL1 Blue MRF' kan a DNA mini-preparation (Riggs, M. G. & McLachlan, A. (1986), A simplified screening procedure for large numbers of plasmid mini-preparation. *BioTechniques* 4, 310-313.) was performed with 24 ampicillin-resistant transformants and positive clones were identified by BamHI restriction analysis. The sequence of the cloned PCR product was confirmed by resequencing using the ABI PRISM Big Dye Terminator Cycle Sequencing Ready Reaction Kit (Perkin-Elmer, Weiterstadt).

The plasmid-DNA of pCR-ASE1 was further restricted with KpnI/SacI and the resulting DNA fragment was ligated into the same restriction site of the dephosphorylated yeast-*E. coli* shuttle-vector pYES2 resulting in pY2ASE1. After transformation of *E. coli* and DNA mini-preparation from the transformants, the orientation of the DNA fragment within the vector was checked. One clone was grown for DNA maxi-preparation with the Nucleobond® AX 500 Plasmid-DNA Extraction Kit (Macherey-Nagel, Düringen).

*Saccharomyces cerevisiae* INVSc1 was transformed with pY2ASE1 and pYES2 by a modified PEG/lithium acetate protocol (Ausubel et al., 1995). After selection on CMdum agar plates containing 2% glucose, four pY2ASE1 transformants and one pYES2 transformant were chosen for further cultivation and functional expression.

b) Functional Expression of Elongase Activity in Yeast

Preculture:

20 ml of CMdum liquid medium containing 2% (w/v) raffinose were inoculated with the transgenic yeast clones (pY2ASE1a-d, pYES2) and grown for 3 days at 30° C., 200 rpm until an optical density at 600 nm ($OD_{600}$) of 1.5-2 was reached.

Main Culture:

For expression 20 ml Cmdum liquid medium with 2% raffinose and 1% (v/v) Tergitol NP-40 was supplemented with the fatty acid to be tested to a final concentration of 0.003% (w/v). The media were inoculated with the precultures to an $OD_{600}$ of 0.05. The expression was induced at an $OD_{600}$ of 0.2 with 2% (w/v) galactose for 16 h, after which time the cultures had reached an $OD_{600}$ of 0.8-1.2.

c) Fatty Acid Analysis

The total fatty acids were extracted from yeast cultures and analyzed by gas chromatography. For this, cells from 5 ml culture were harvested by centrifugation (1000×g, 10 min., 4° C.) and washed once with 100 mM NaHCO$_3$, pH 8.0 to remove residual medium and fatty acids. For preparation of the fatty acid methyl esters (FAMES) the cell pellets were treated with 1 N methanolic H$_2$SO$_4$ and 2% (v/v) dimethoxypropane for 1 h at 80° C. The FAMES were extracted twice with 2 ml petroleum ether, washed once with 100 mM NaHCO$_3$, pH 8.0 and once with distilled water and dried with Na$_2$SO$_4$. The organic solvent was evaporated under a stream of argon and the FAMES were dissolved in 50 µl of petroleum ether. The samples were separated on a ZEBRON ZB-Wax capillary column (30 m, 0.32 mm, 0.25 µm; Phenomenex) in a Hewlett Packard 6850 gas chromatograph with a flame ionization detector. The oven temperature was programmed from 70° C. (1 min. hold) to 200° C. at a rate of 20° C./min., then to 250° C. (5 min. hold) at a rate of 5° C./min and finally to 260° C. at a rate of 5° C./min. Nitrogen was used as carrier gas (4.5 ml/min. at 70° C.). The fatty acids were identified by comparison with retention times of FAME standards (SIGMA).

Fatty acid patterns of transgenic yeast strains are shown in Tab. 2 retention times as the fed/incorporated fatty acid. A gas chromatography/mass spectroscopy can give additional support to confirm its identity.

FIG. 3A-D shows essentially a GC graph of data presented in Table 2. Explanation to FIG. 3A-D:

GC chromatograms of fatty acid methyl esters extracted from transgenic yeast containing pY2ASE1. Yeast cultures were grown in the presence (indicated by an asterisk) or absence of exogenous fatty acids. Exogenous fatty acids (in the form of sodium salts) were LA (linoleic acid; 18:2 Δ$^{9, 12}$; 18:2 n-6, see FIG. 3B), ALA (α-linolenic acid; 18:3 Δ$^{9, 12, 15}$; 18:3 n-3, see FIG. 3A), GLA (γ-linolenic acid; 18:3 Δ$^{6, 9, 12}$; 18:3 n-6, see FIG. 3C) or no substrate (FIG. 3D). FIG. 3B represents expression of the ASE1 ORF as induced by the addition of galactose. After 24 h, yeast cells were harvested by centrifugation, washed to remove exogenous substrate and methylated. Fatty acid methyl esters were separated and detected using standard methods and peaks identified by comigration of known standards. It is clear that Ig_ASE1 encodes a Δ9-C$_{18}$-PUFA-specific elongating activity. Identified products show that nucleotide sequence of Ig_ASE1

TABLE 2

Fatty acid patterns in mol % of transgenic yeast strains

| Induction | −Substrate | | +LA (18:2 n − 6) | | +ALA (18:3 n − 3) | | +GLA (18:3 n − 6) | |
|---|---|---|---|---|---|---|---|---|
| | +gal | −gal | +gal | −gal | +gal | −gal | +gal | −gal |
| 16:0 | 28.7 | 30.2 | 27.0 | 28.9 | 26.6 | 28.9 | 30.0 | 31.0 |
| 16:1 n − 9 | 41.6 | 42.4 | 30.7 | 25.4 | 30.1 | 26.4 | 24.3 | 24.6 |
| 18:0 | 6.8 | 6.1 | 5.7 | 5.8 | 6.3 | 6.3 | 6.8 | 6.2 |
| 18:1 n − 9 | 22.9 | 21.3 | 16.5 | 13.4 | 18.4 | 16.6 | 14.7 | 13.4 |
| 18:2 n − 6* | — | — | 11.0 | 26.5 | — | — | — | — |
| 18:3 n − 6* | — | — | — | — | — | — | 24.2 | 24.8 |
| 18:3 n − 3* | — | — | — | — | 10.2 | 21.8 | — | — |
| 20:2 n − 6 | — | — | 9.1 | — | — | — | — | — |
| 20:3 n − 3 | — | — | — | — | 8.4 | — | — | — |
| % Elongation | 0 | — | 45.3 | — | 45.2 | — | 0 | — |

Explanation to Tab. 2:

Fatty acid elongation of different substrates supplied to transgenic yeast containing pY2ASE1. Exogenous fatty acids supplied as substrates for elongation are indicated by an asterisk [*]. The values given are expressed as mol % of total fatty acid methyl esters identified by GC and FID. In the case of elongated substrates, this is also expressed as a % conversion. Expression of the ASE1 transgene was induced by the addition of galactose. Only C18 substrates with a double bond at the Δ9 position were elongated by the ASE1 open reading frame. All values represent the mean of three separate experiments.

GC analysis of FAMES prepared from total lipids of the yeasts transformed with pY2ASE1 and grown in the presence of different exogenous fatty acids (ALA, GLA, LA), and their fatty acid patterns are shown in mol % in Table 1. The incorporation of GLA does not yield any elongation product di-homo-GLA (20:3 d8,11,14) while ALA is elongated to yield C20:3 d11,14,17, and LA is elongated to yield C20:2 d11, 14.

The transgenic yeast clones transformed with pY2ASE1 and supplied with exogenous substrates show an additional peak in the gas chromatogram (identified by an asterisk [*] in FIGS. 3A-D), which has been identified by comparison of codes for a Δ9-selective C$_{18}$ fatty acid elongase from the alga *Isochrysis galbana*, which leads to the formation of new fatty acids in transgenic yeasts.

Further feeding experiments with several other fatty acids can be performed to confirm the substrate selectivity of this elongase in further detail.

Example 15

Purification of the Desired Product from Transformed Organisms in General

Recovery of the desired product from plant material or fungi, algae, ciliate cells or supernatant of the above-described cultures can be performed by various methods well known in the art. If the desired product is not secreted from the cells, the cells can be harvested from the culture by low-speed centrifugation, the cells can be lysed by standard techniques, such as mechanical force or sonification. Organs of plants can be separated mechanically from other tissue or organs. Following homogenization cellular debris is removed by centrifugation, and the supernatant fraction containing the soluble proteins is retained for further purification of the desired compound. If the product is secreted from desired cells, then the cells are removed from the culture by low-speed centrifugation, and the supernatant fraction is retained for further purification.

The supernatant fraction from each purification method is subjected to chromatography with a suitable resin, in which the desired molecule is either retained on the chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There are a wide array of purification methods known in the art and the preceding method of purification is not meant to be limiting. Such purification techniques are described, for example, in Bailey, J. E. & Ollis, D. F. Biochemical Engineering Fundamentals, McGraw-Hill: N.Y. (1986).

The identity and purity of the isolated compounds may be assessed by techniques standard in the art. These include high-performance liquid chromatography (HPLC), spectroscopic methods, staining methods, thin layer chromatography, NIRS, enzymatic assays, or microbiological assays. Such analysis methods are reviewed in: Patek et al. (1994) *Appl. Environ. Microbiol.* 60: 133-140; Malakhova et al. (1996) *Biotekhnologiya* 11: 27-32; and Schmidt et al. (1998) *Bioprocess Engineer.* 19: 67-70. Ullmann's Encyclopedia of Industrial Chemistry, (1996) vol. A27, VCH: Weinheim, p. 89-90, p. 521-540, p. 540-547, p. 559-566, 575-581 and p. 581-587; Michal, G. (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

EQUIVALENTS

Those skilled in the art will recognize, or will be able to ascertain using no more than routine experimentation, many equivalents to the specific embodiments of the invention described herein. Such equivalents are intended to be encompassed by the claims.

We claim:

1. An isolated nucleic acid comprising a nucleotide sequence which encodes a polypeptide which elongates α-linolenic acid ($C_{18:3\ \Delta 9,\ 12,\ 15}$) by at least two carbon atoms whereas γ-linolenic acid ($C_{18:3\ \Delta 6,\ 9,\ 12}$) is not elongated, selected from the group consisting of:
   a) the nucleic acid sequence of SEQ ID NO: 1;
   b) a nucleic acid sequence which encodes the polypeptide of SEQ ID NO: 2; and
   c) a derivative of the nucleic acid sequence of SEQ ID NO: 1, which encodes a polypeptide having at least 95% homology with the nucleic acid sequence encoding the amino acid sequence of SEQ ID NO: 2.

2. The isolated nucleic acid as claimed in claim 1, which is derived from a plant.

3. The isolated nucleic acid as claimed in claim 1, which is derived from the genus *Isochrysis*.

4. A gene construct comprising the isolated nucleic acid sequence as claimed in claim 1, functionally linked to one or more regulatory signals.

5. The gene construct as claimed in claim 4, further comprising a fatty acid biosynthesis gene.

6. The gene construct as claimed in claim 5, wherein the fatty acid biosynthesis gene is selected from the group consisting of Δ19-, Δ17-, Δ15-, Δ12-, Δ9-, Δ8-, Δ6-, Δ5-, Δ4-desaturase, hydroxylase, elongase, Δ12-acetylenase, Acyl-ACP-thioesterasen, β-ketoacyl-ACP-synthase and β-ketoacyl-ACP-reductase.

7. A vector comprising a nucleic acid as claimed in claim 1, or a gene construct comprising said nucleic acid.

8. A plant cell comprising at least one heterologous nucleic acid as claimed in claim 1.

9. A plant comprising the plant cell of claim 8.

10. The plant of claim 9, which is a transgenic plant.

11. An antisense nucleotide sequence which is fully complementary to a nucleotide sequence selected from the group consisting of:
   a) the nucleic acid sequence of SEQ ID NO: 1;
   b) a nucleic acid sequence which encodes the polypeptide of SEQ ID NO: 2; and
   c) a derivative of the nucleic acid sequence of SEQ ID NO: 1, which encodes a polypeptide having at least 95% homology with the nucleic acid sequence encoding the amino acid sequence of SEQ ID NO: 2; and wherein said polypeptide elongates α-linolenic acid ($C_{18:3\ \Delta 9,\ 12,\ 15}$) by at least two carbon atoms whereas γ-linolenic acid ($C_{18:3\ \Delta 6,\ 9,\ 12}$) is not elongated.

12. An isolated nucleic acid comprising SEQ ID NO: 1.

13. An amino acid sequence comprising SEQ ID NO: 2.

* * * * *

UNITED STATES PATENT AND TRADEMARK OFFICE
CERTIFICATE OF CORRECTION

PATENT NO. : 7,601,889 B2 Page 1 of 1
APPLICATION NO. : 10/472321
DATED : October 13, 2009
INVENTOR(S) : Napier et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 344 days.

Signed and Sealed this

Fourteenth Day of December, 2010

David J. Kappos
*Director of the United States Patent and Trademark Office*